United States Patent
Whitehurst

(10) Patent No.: US 11,728,030 B2
(45) Date of Patent: Aug. 15, 2023

(54) METHODS OF TREATMENT AND DIAGNOSIS USING ENHANCED PATIENT-PHYSICIAN COMMUNICATION

(71) Applicant: Apple Inc., Cupertino, CA (US)

(72) Inventor: Todd K. Whitehurst, Lithia, FL (US)

(73) Assignee: Apple Inc., Cupertino, CA (US)

( * ) Notice: Subject to any disclaimer, the term of this patent is extended or adjusted under 35 U.S.C. 154(b) by 960 days.

(21) Appl. No.: 14/998,287

(22) Filed: Dec. 23, 2015

(65) Prior Publication Data

US 2016/0210416 A1 Jul. 21, 2016

Related U.S. Application Data

(60) Provisional application No. 62/096,091, filed on Dec. 23, 2014.

(51) Int. Cl.
| | |
|---|---|
| *G16H 40/63* | (2018.01) |
| *G16H 10/65* | (2018.01) |
| *G16H 40/67* | (2018.01) |
| *G16H 80/00* | (2018.01) |

(52) U.S. Cl.
CPC ............ *G16H 40/63* (2018.01); *G16H 10/65* (2018.01); *G16H 40/67* (2018.01); *G16H 80/00* (2018.01); *Y02A 90/10* (2018.01)

(58) Field of Classification Search
CPC combination set(s) only.
See application file for complete search history.

(56) References Cited

U.S. PATENT DOCUMENTS

| | | |
|---|---|---|
| 6,820,057 B1 | 11/2004 | Loch et al. |
| 8,005,691 B2 | 8/2011 | Kumar et al. |
| 8,423,387 B1 | 4/2013 | Mirza |

(Continued)

FOREIGN PATENT DOCUMENTS

| | | |
|---|---|---|
| CN | 101393520 A | 3/2009 |
| CN | 101667224 A | 3/2010 |

(Continued)

OTHER PUBLICATIONS

U.S. Appl. No. 15/014,856, "Non-Final Office Action", dated Nov. 15, 2018, 17 pages.

(Continued)

*Primary Examiner* — Lena Najarian
(74) *Attorney, Agent, or Firm* — Kilpatrick Townsend & Stockton LLP

(57) ABSTRACT

Methods of treatment and diagnosis using facilitated communication of health information from a patient device to a physician device are provided herein. Methods include improved dissemination and management of health information data while safeguarding patient privacy. A patient may initiate a tele-medicine session for treatment using a portable user device of the patient, after which a physician may request a set of data through the patient device relevant to the treatment. In response, the device of the patient identifies a subset of the data set requested by the physician that is authorized by the patient for release to the physician. The system further facilitates display of differing types of information on a user interface of the physician's device to facilitate improved treatments and diagnostics, health information collection and patient follow-up.

38 Claims, 20 Drawing Sheets

(56) References Cited

U.S. PATENT DOCUMENTS

| | | |
|---|---|---|
| 8,715,181 B2 | 5/2014 | Brynelsen et al. |
| 8,737,971 B2 | 5/2014 | van Rooyen et al. |
| 2001/0032100 A1 | 10/2001 | Mahmud et al. |
| 2001/0037219 A1* | 11/2001 | Malik ................ G06F 19/3418 705/2 |
| 2002/0005935 A1 | 1/2002 | Robin |
| 2003/0028400 A1 | 2/2003 | Christ et al. |
| 2003/0074221 A1 | 4/2003 | Christ et al. |
| 2004/0054760 A1 | 3/2004 | Ewing et al. |
| 2004/0162466 A1* | 8/2004 | Quy ..................... G06F 19/321 600/300 |
| 2005/0049898 A1 | 3/2005 | Hirakawa |
| 2006/0064030 A1* | 3/2006 | Cosentino ............ A61B 5/0031 600/547 |
| 2006/0248593 A1 | 11/2006 | Dennis et al. |
| 2006/0277076 A1* | 12/2006 | Hasan .................. G06F 19/324 705/3 |
| 2007/0299316 A1* | 12/2007 | Haslehurst ........... A61B 5/0002 600/300 |
| 2008/0120707 A1* | 5/2008 | Ramia ................ H04L 63/0861 726/5 |
| 2011/0295616 A1 | 12/2011 | Vesto |
| 2012/0101847 A1 | 4/2012 | Johnson et al. |
| 2013/0064358 A1 | 3/2013 | Nusbaum |
| 2013/0197942 A1 | 8/2013 | Chiu et al. |
| 2013/0275151 A1 | 10/2013 | Moore et al. |
| 2013/0304511 A1 | 11/2013 | Gunter |
| 2014/0081662 A1 | 3/2014 | Bradrick et al. |
| 2014/0122125 A1 | 5/2014 | Deshpande et al. |
| 2014/0172442 A1* | 6/2014 | Broderick .............. G16H 20/30 705/2 |
| 2014/0242698 A1 | 8/2014 | Smith |
| 2014/0257851 A1 | 9/2014 | Walker et al. |
| 2014/0276552 A1 | 9/2014 | Nguyen, Jr. et al. |
| 2014/0278474 A1 | 9/2014 | Mcclure et al. |
| 2015/0242592 A1 | 8/2015 | Weiss et al. |
| 2015/0244852 A1 | 8/2015 | Erickson et al. |
| 2015/0347499 A1 | 12/2015 | Keen et al. |
| 2015/0347684 A1 | 12/2015 | Keen et al. |
| 2015/0347690 A1 | 12/2015 | Keen et al. |
| 2015/0347784 A1 | 12/2015 | Keen |
| 2016/0301792 A1 | 10/2016 | Lee et al. |
| 2017/0011182 A1 | 1/2017 | Whitehurst |

FOREIGN PATENT DOCUMENTS

| | | | |
|---|---|---|---|
| CN | 103182175 A | 7/2013 | |
| WO | WO-2012173541 A1 * | 12/2012 | ......... H04L 67/1095 |
| WO | 2015183495 | 12/2015 | |

OTHER PUBLICATIONS

"Office Action", China Patent Application No. 201580028726.9, dated Jul. 31, 2017, 15 pages.

* cited by examiner

| | 502 | 504 | 506 | 508 | 510 |
|---|---|---|---|---|---|
| | DATA TYPE | VALUE | AUTHORIZED? | REQUESTED? | Result on Data Requested by Physician Y |
| 512 | Heart Rate | 78 | YES | YES | 78 |
| 514 | Glucose | 90 | Range Only | YES | normal |
| 516 | Weight | 198 | Physician X Only | YES | [] |
| 518 | Steps | 82 | Primary Only | YES | [] |
| 520 | HIV | 1 | NO | YES | [] |
| 522 | Activity Level | Low | Prompt Each Time | NO | [] |

PHYSICIAN has requested health information for session 1 (bug bite):

CHECK TO AUTHORIZE RELEASE TO: PHYSICIAN

- ☐ Name    ☐ Age    ☐ Sex    ☐ Insurance
- ☑ ▷ Vital Signs
  - ☑ heart rate    ☑ pulse
  - ☑ respiratory rate    ☑ body temperature
- ☑ Weight
- ☐ ▷ Activity Level
- ☐ Family History
  - ☐ heart disease    ☐ mental illness    ☐ cancer
- ☑ ▷ Medications
  - ☑ Antibiotics
  - ☑ HIV
  - ☑ Cold
  - ☑ Statins
- ☐ ▷ Current Conditions
  - ☐ HIV
  - ☐ Arthritis
  - ☐ Gout
  - ☐ Acne

- ☐ Select All
- ☐ Sensor Data
- ☐ Option 1
- ☐ General
- ☑ PHYSICIAN
- ☐ DR.
- ☐ HIV related
- ☐ Anonymous Option

[ Confirm/Send ]    [ Cancel ]    [ Message ]

| Patient Name & Birthdate | Interactive Video |
|---|---|
| Conditions and Diagnoses<br>• Diabetes (diagnosed 2008)<br>• Neck injury (1 month ago)<br>Medications and Drug Allergies<br>• Metformin 500 mg orally twice a day | |
| <u>Data from Patient's</u> ▶<br>*Click arrow to display available fields* | |

*No Patient Health Info has been retrieved from the Patient*

| Diagnosis | Physician Notes |
|---|---|
| • Diabetes | • Neck injury is under care of orthopedic surgeon |

Medication Changes: Continue on Metformin 500 mg twice a day (6 refills @ Walgreens)
Lab Tests Requested: HbA1c
Additional Treatments and Procedures Requested: None

| Patient Name & Birthdate | Interactive Video |
|---|---|
| Conditions and Diagnoses<br>• Diabetes (diagnosed 2008)<br>• Neck injury (1 month ago)<br>Medications and Drug Allergies<br>• Metformin 500 mg orally twice a day<br><u>Data from Patient's</u> ▶<br>*Click arrow to display available fields* | |

● 108 ● 65 ♥ 85 >
March 29, 2013, 2:45 PM

♥ 71 BPM >
July 15, 2013, 4:39 PM 164.5 LB     BMI 22.1 >
June 8th, 6:30 AM

Blood Pressure — February, March, April

Heart Rate — JULY 3 4 5 6 7 9 15

Weight — March April May

| Diagnosis | Physician Notes |
|---|---|
| • Diabetes | • Neck injury is under care of orthopedic surgeon |

Medication Changes: Continue on Metformin 500 mg twice a day (6 refills @ Walgreens)
Lab Tests Requested: HbA1c
Additional Treatments and Procedures Requested: None

*FIG. 12C*

METHODS OF TREATMENT AND DIAGNOSIS USING ENHANCED PATIENT-PHYSICIAN COMMUNICATION

CROSS REFERENCES TO RELATED APPLICATIONS

The present application claims the benefit under 35 USC § 119(e) of U.S. Provisional Appln. No. 62/096,091 filed Dec. 23, 2014; the full disclosure which is incorporated herein by reference in its entirety.

The present application is related to U.S. application Ser. No. 14/499,449 filed Sep. 29, 2014 entitled Managing User Information—Authorization Masking; U.S. application Ser. No. 14/499,461 filed Sep. 29, 2014 entitled Managing User Information—Background Processing; U.S. application Ser. No. 14/499,512 filed Sep. 29, 2014 entitled Managing User Information—Data Type Extension; and U.S. application Ser. No. 14/499,519 filed Sep. 29, 2014 entitled Managing User Information—Source Prioritization; the entire contents of each are hereby incorporated by reference for all purposes.

FIELD OF INVENTION

The present invention relates to methods of treatments and diagnosis using enhanced communication between physician and patient.

BACKGROUND OF THE INVENTION

Medical treatments and diagnostics in the modern healthcare system often involve exchanges of a multitude of patient information and medical records to various health care providers for each patient. Current health care systems can be complex and fragmented resulting in redundancies and inefficiencies in collecting data that frustrate both patient and physician and delay diagnosis and treatment. Although the development of electronic medical records has improved exchange of information somewhat, health information within the electronic medical record is limited and must be updated periodically. In recent years, acquisition of health information and various health metrics outside of the electronic medical records has increased dramatically. The usefulness of such health information, however, is limited given the complexities and burden associated with dissemination of such large amounts of information. While treatments and diagnostics could be improved by utilizing the wide range of health information now available, providing such improvement is challenging and often problematic given the limited time and resources available in modern healthcare in addition to heightened concerns in regard to patient privacy.

BRIEF SUMMARY OF THE INVENTION

Methods of the present invention pertain to facilitating treatment and/or diagnosis of a patient by facilitated communication between the physician and patient. In particular, systems and methods relate to facilitating communication of health information including a plurality of health data elements relating to the patient received by a portable computing device of the patient to the physician. Methods include sending to the physician, with the a portable computing device of the patient, a subset of a set of data of the plurality of health data elements requested by the physician, the subset being data authorized by the patient for sending to the physician.

In some embodiments, a first portable computing device of a patient receives a plurality of health data elements relating to the patient and initiating communication with a first physician with the portable computing device of the patient, typically in response to an input by the patient. In response to the initiating physician communication, the first portable device receives a health information query from the first physician, typically from a second computing device associated with the first physician. The health information query includes a request of a first set of data of the plurality of health data elements, the first set of data being associated with the treatment and/or diagnosis of the patient by the first physician. In response, the first portable computing device identifies a first subset of the plurality of health data elements that is authorized by the patient for communication to the first physician and outputs to the first physician, the first subset of the first set of data that excludes a second subset of the first set of data so as to facilitate the treating and/or the diagnosis of the patient by the first physician.

In some aspects, the method includes receiving a command with the first portable computing device input by the patient and/or a patient caretaker to initiate communication with the first physician. Such methods may include the step of selecting the plurality of health data elements, with the first portable computing device, corresponding to the patient for whom communication with the physician is desired. For example, differing sets of health data elements, each corresponding to a different patient, may be access by a single portable computing device, such as a single device accessing a first set of health information relating to a first individual and second set of health information relating to another individual, such as a child or dependent. This aspect allows a parent to initiate a physician communication for their child and facilitates communication of health data relating to the child using the portable computing device of the parent.

In another aspect, methods includes steps of selecting the physician for which the patient desires to initiate communication or selecting a condition for which the patient desired to be treated and/or diagnosed. In one example, the method includes a step of receiving a selection of the first physician from a plurality of physicians displayed on a graphical user interface of the first portable device. In some embodiments, the method may include displaying a plurality of physicians on a graphical user interface of the first portable device based on the input condition.

In some aspects, the health data includes a plurality of health data elements including any of: input or downloaded data, sensor data and laboratory values. Input or downloaded data comprises data input by the patient and/or received from an electronic medical record, which may include any or all of: age, race, sex, weight, height, family history, and vaccination history.

In some embodiments, a system in accordance with the invention includes one or more sensor devices for obtaining sensor data such that receiving the plurality of health data elements comprises receiving sensor data from one or more sensor devices communicatively coupled with the portable computing device. In some aspects, the system is configured to obtain the sensor data from the one or more sensor devices over a duration of time. The one or more sensor devices may include one or more wearable devices that are wearable by the patient, each including a sensor that measures a health metric of the patient when worn by the patient. The health metric corresponds to any of an activity level, activity tracking, body temperature, heart wellness data, hydration levels, perspiration, blood glucose, salinity, sleep cycles, posture, $O_2$ levels, muscle engagement, or any combination thereof. In some embodiments, the health metric corresponds to blood glucose that is monitored by a wearable device such that the plurality of health data elements include blood glucose measurements obtained multiple times each day over the duration of time, the duration of time being one week or more, so as to facilitate treatment of diabetes.

In some embodiments, the sensor data is received from the one or more sensor devices automatically over the duration of time without requiring an additional input from the patient to receive the at least some health data elements. In certain aspects, at least some of the plurality of health data elements are not specific to the health condition being treated and/or diagnosed. In certain other aspects, at least some of the plurality of health data elements are automatically received regardless of whether the patient initiates communication for treatment and/or diagnosis of any particular condition or treatment.

In some embodiments, methods include establishing communication between a first portable computing device associated with the patient and second computing device associated with a first physician. Communication may be established remotely through a server and/or through near field communication. The second computing device may also be communicatively coupled with an electronic medical record associated with the patient, and wherein the outputting of the first subset of health data elements is performed so that the second subset of the first set of data remains excluded from the electronic medical record. In some embodiments, the second computing device is a portable computing device, which includes a user input for receiving input from the physician or associated medical personnel from which the first set of data for the health data query is determined. In some embodiments, the input may include receiving a selection, on the second portable computing device, of the first set of data from a group of pre-selected sets of data requests based on a medical sub-specialty of the first physician. Alternatively or in addition, the input may include an individual selection of one or more indicators corresponding to one or more health data elements within the first set of data displayed on a graphical user interface of the second computing device. In some embodiments, the first set of data in the health information query is determined based on receiving of a categorical selection input by the physician with the second computing device, the categorical selection being selected from categories. The categories may include a specialty or sub-specialty, a medication or class of medication, and a condition or class of conditions for which the patient is being diagnosed and/or treated. The condition may include any of: a symptom, an injury, a disability, a disorder, a syndrome, an infection, dysfunction, pain or a disease. The class or type of medication may be grouped according to any of: chemical structure, mechanism of action, and purpose.

In some embodiments, methods include determining the first set of data being requested in the health data query based, at least in part, on one or more attributes of the patient, the attribute comprising one or more of: a risk factor associated with a condition being diagnosed and/or treated, a drug allergy, age, weight, gender, race, geographical location, ethnic background, a previously diagnosed condition, and a disease state. The one or more attributes of the patient can be received by the second computing device from an electronic medical record of the patient, input by the physician, and/or from the plurality of health data elements. The one or more attributes of the patient can be received by the second computing device of the physician from one or both of the electronic medical record of the patient and the plurality of health data elements upon initiation of communication with the first physician.

In some embodiments, the second computing device associated with the physician is configured with a user input and/or a graphical user interface that allow the physician to select the first set of data being requested in the health information query. In such embodiments, the methods may include a step of: displaying a set of selectable options on a graphical user interface of the second computing device from which the first set of data is determined, the set of selectable options being determined in part based on the one or more attributes of the patient received by the second computing device. The first set of data includes any of: a patient's vital signs, one or more physiological measurements of the patient, a medication of the patient, a factor associated with the condition to be treated or diagnosed, or any combination thereof.

In some embodiments, the first computing device associated with the patient is configured with a user input and/or a graphical user interface that allows the patient or an associated caretaker to select the first subset of data and/or authorize release of the identified first subset of data to the physician. In such embodiments, the method may include a step of identifying the first subset of data based on a patient selection input by the patient or on a pre-selection accessed by the first portable computing device. For example, the first portable computing device may display on a graphical user interface of the first portable computing device the first set of data requested in the health information query; and receive a user input with the first portable computing device authorizing output of the first subset of data to the first physician. In another example, the first computing device may receive a selection of the first subset of data from the first set of data displayed on the graphical user interface, the selection being received through the graphical user interface. The selection may be a categorical selection by a user selected from a plurality of categories displayed on the graphical user interface. The categories may relate to any of a previously diagnosed condition, an attribute of the patient, a family history of the patient, a medication currently or previously prescribed the patient, a characteristic of the physician from which the query is received, or any combination thereof.

In one aspect, the attribute of the patient can include any of: weight, age race, activity level, diet, sleep, or any combination thereof. In addition, the plurality of health data elements further includes processed data relating to a health metric. The processed data may be provided by a third-party application with the first portable computing device based, in part, on other health data elements of the plurality received by or stored on the portable computing device. In another aspect, input may be utilized to select the first physician from a plurality of physician displayed on the graphical user interface or to select a second physician for treatment and/or diagnosis of a same or different condition as the communication with the first physician. Such methods may include steps of: receiving a selection of the first physician with a graphical user interface of the first portable device; receiving a selection of the second physician with the graphical user interface of the first portable device subsequent receiving the selection of the first physician, wherein the first physician and second physician are selected for treatment and/or diagnosis of a same or different condition. In such methods, the first subset of data of the first set of data and the first subset of the second set of data may be non-mutually exclusive such that the subsets may be overlapping or non-overlapping. In certain aspects, the identifying of the first subset of the first set and the second set of data differs based on which of the first and second physicians the health information query is received from.

In some embodiments, methods include initiating a communication with a second physician after the communication and health information exchange with the first physician. Such methods may include the same and/or similar steps of identifying a first subset of a set of data requested by the second physician and facilitating communication and exchange of the first subset of data authorized by the patient with the second physician. For example, such methods may include a steps of: initiating communication with a third computing device associated with a second physician with the first portable computing device; receiving, with the portable computing device, a health information query from the second physician, the health query requesting a second set of data from the plurality of health data elements that is associated with the treatment and/or diagnosis of the patient by the second physician, the second set of data being different from the first set of data; identifying, with the first portable computing device, a first subset of the second set of data that is authorized by the patient for communication to the second physician; and outputting to the second physician, with the first portable computing device of the patient, the first subset that excludes a second subset of the second set of data so as to facilitate the treating and/or the diagnosis of the patient by the second physician.

Systems for facilitating communication and exchange of health information data between a patient and physician are also provided. Example embodiments of such systems include: a first portable computing device operable by the patient or an associated caretaker, the first portable computing device including a wireless communication module for transmitting to and receiving data from the physician; a health information database accessible by the first portable computing device, wherein the patient information database includes a plurality of health data elements associated with the first patient; and a processor of the portable computing device, the processor having a computer readable medium having stored thereon computer executable instructions configured to facilitate communication and exchange of health information data between the physician and patient in accordance with any of the methods described herein. For example, the process may be configured to: initiate communication with the first physician using the communication module; receive a health information query from the first physician requesting a first set of data of the plurality that is associated with the treating and/or diagnosis by the first physician; identify a first subset of the first set of data that is authorized by the patient for communication to the first physician; and output to the physician from the health information database the first subset of the first set of data that excludes a second subset of the first set of data.

In some embodiments, the system includes one or more sensor devices adapted to obtain sensor data and are communicatively coupled with the first portable computing device such that the plurality of health data elements include sensor data from the one or more sensor device. The one or more sensor devices are configured to obtain sensor data relating to any of: activity level, activity tracking, respiration, body temperature, heart wellness data, hydration levels, perspiration, blood glucose, salinity, sleep cycles, posture, $O_2$ levels, muscle engagement, or any combination thereof. In some embodiments, the one or more sensor devices are configured to obtain sensor data over a duration of time and the processor is configured such that the sensor data is obtained automatically over the duration of time. The one or more sensor devices may include one or more wearable sensor devices that may be separate from or incorporated into the first portable computing device of the patient. The one or more sensor devices include one or more wearable devices that are wearable by the patient, each including a sensor that measures a health metric of the patient when worn by the patient.

In some embodiments, each of the first portable computing device and the second computing device may include a user input and/or a graphical user interface that allows the patient and physician, respectively, to select and/or authorize the first subset of the first set of requested data and the first set of data in the health information query. For example, the second computing device may be configured to display a set of selectable options on a graphical user interface of the second computing device from which the first set of data is determined, the set of selectable options being determined in part based on the one or more attributes of the patient received by the second computing device.

In some aspects, the system may include a third computing device associated with a second physician configured to facilitate communication and exchange of health information data between the patient and the second physician in the same or similar fashion as the second computing device described herein.

BRIEF DESCRIPTION OF THE DRAWINGS

FIG. 5 is simplified data structure diagram illustrating at least some information associated with managing information between patient and physician, in accordance with certain embodiments.

FIGS. 10A-10D illustrate sequential views of a patient device during a tele-medicine session with a physician, in accordance with certain embodiments.

FIGS. 12A-12D illustrate sequential views of a physician device during a tele-medicine session with a physician, in accordance with certain embodiments.

DETAILED DESCRIPTION OF THE INVENTION

Figure 1:
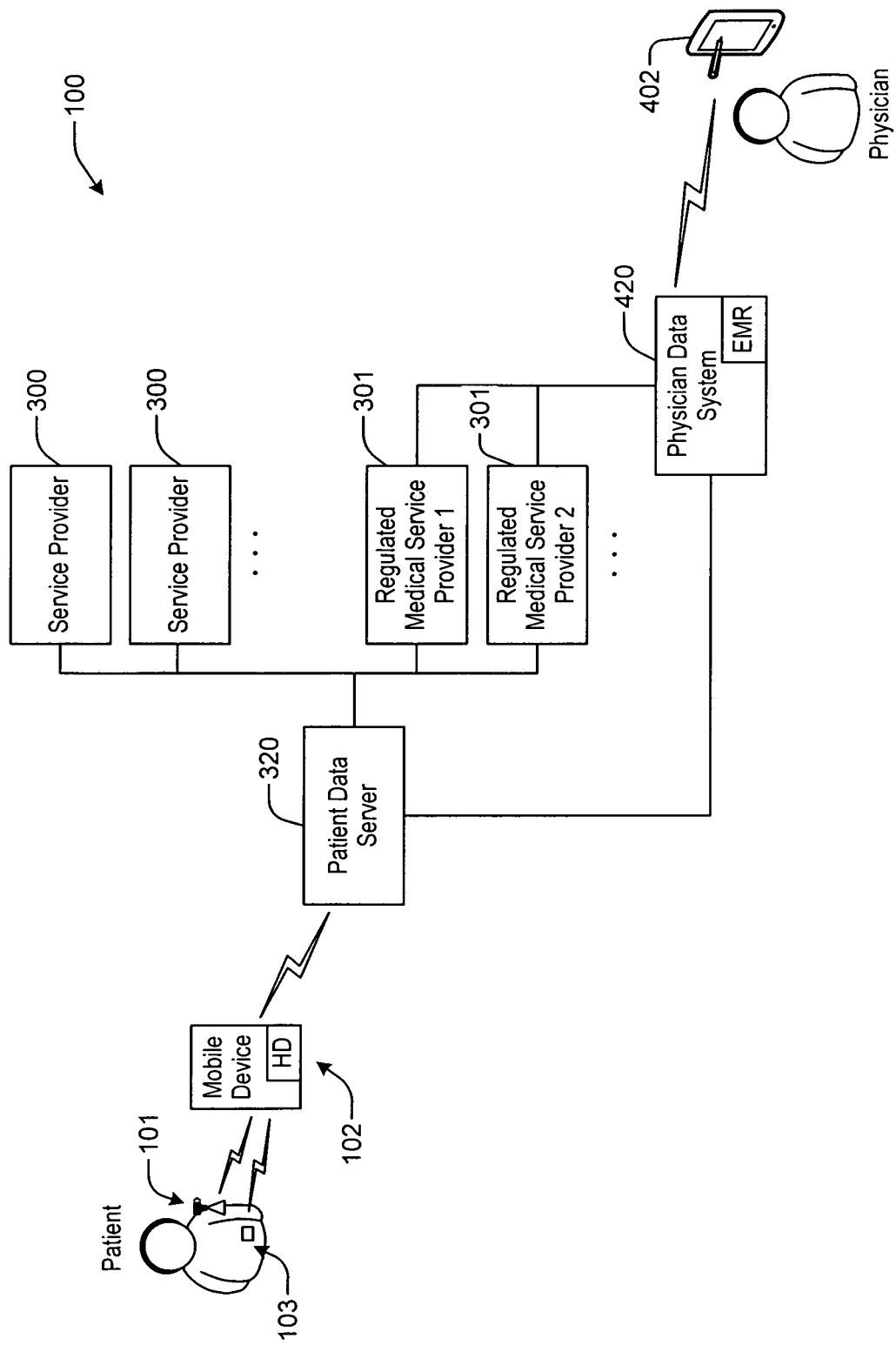
FIG. 1 is a simplified block diagram illustrating a system for treating and/or diagnosing a patient using enhanced patient-physician communication in accordance with certain embodiments of the present invention.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified so as not to obscure the example being described.

Embodiments of the present disclosure provide improved methods of treatment and diagnosis with enhanced patient physician communication such that treatment and diagnosis utilizes health information obtained by the patient (e.g., personal information collected by one or more wearable sensor devices and/or stored in a portable electronic device of the patient) that would otherwise likely be too burdensome to obtain with conventional methods. In some embodiments, a system is provided by which communication between the patient and physician is enhanced such that relatively large sets of data relevant to a treatment can be requested from the patient and obtained by the physician within a few minutes or less, often without requiring any interrogation between patient and physician. In addition, the system allows use of third-party applications on a portable device of the patient to provide, monitor and/or track health information or various health metrics for the patient's use and which can be selectively communicated to the physician as needed. In some embodiments, the system is configured to facilitate requests for specific sets of data as desired by physician. In return, the patient device delivers a subset of data of the requested set to the physician based on an identification of data authorized by the patient to be sent to the physician. Such a system allows requesting and communication of health information outside of the patient's electronic medical record to the physician, while maintaining the patient's privacy as to a subset of the data requested, thereby improving treatment and diagnosis by utilizing only relevant personal health information obtained by the patient through their personal device. This communication can be performed in a single electronic exchange between physician and the patient, typically without requiring any oral dialogue directly between patient and physician. Embodiments of the system allow the physician access to particular data types of the patient's health information based, at least in part, on an authorization from the user associated with the data and a request for specific data from the physician.

According to certain embodiments, the method may also cause a computer system to enable storage on a patient device and/or access of health information associated with differing types of data and to determine whether the data is authorized for release to a particular physician or medical facility or to a device or third-party application associated therewith. In some embodiments, the computer system identifies a first specific set of data being requested for use by a physician, which may be communicated to the portable device of the patient directly (e.g. near range communication) or remotely (e.g. through a server using a first-party framework or application, or a third-party application of the device). The method may also cause the computer system to provide data to the user device that identifies information about the requested specific set of data and to query the user in regard to its release or apply a default or pre-selection authorization automatically in response to the requested first set of data.

In one aspect, the system may be implemented as a computing device configured with a memory and a processor. The processor may be configured to execute instructions stored on the memory to configure the memory to identify whether health information data stored on the memory or accessed by the device is patient authorized data, and to communicate specific data that corresponds to a first subset of data of a first set of specific data requested by the physician. In addition, the processor may be configured such that a second subset of data of the first set of specific data, which is not patient authorized data, is excluded from the communication so that the second subset is not sent to the physician as well as excluded from the patient's electronic medical record. In some embodiments, the first subset of data may be communicated in a format so that the physician cannot identify whether a second subset of data is being excluded. For example, indicators of certain fields of the first set of data requested for which there is data in the second subset may be returned in the same manner as if there was no data for those requested data fields (e.g. use of a blank field or a common indicator). This aspect further safeguards patient privacy by avoiding speculation as to the presence of the second subset of data being excluded.

According to another embodiment, a computer-readable medium may include instructions that, when executed, configure a computer processor to receive, from a service provider, instructions for implementing a background process configured to manage authorization and release of various types of data. The instructions may further configure the processor to receive, from the service provider, a data download that includes information about a new data type. The instructions may also configure the processor to receive, from an application, a request to access data corresponding to the data type, and provide, to the application, the data corresponding to the data requested based at least in part on interpreting the received data download.

Embodiments of the present disclosure are directed to, among other things, managing personal information received from external sources, or from other peripheral devices of a user. In some examples, the information collected by the data collection devices may be provided to a user device of the patient (e.g., a mobile phone, a tablet computer, a laptop computer, a wearable computing device, etc.) and/or one or more first-party or third-party applications of the user patient device, before being selectively transmitted to a physician for a treatment. In some examples, a first-party application may be one that is provided with the operating system (O/S) of the user device, is configured to operate natively with the user device, provided by the developers of the O/S for use with the user device, and/or trusted by the O/S and/or device. A third-party application may be one that is provided by a third-party or entity other than the developer/manufacturer of the user device and/or it's O/S. Examples of information being collected and/or managed may be health, fitness, and/or activity information of the user (e.g., blood glucose levels, weight, height, calories burned, heart rate, etc.). The user information may be categorized or otherwise identified by one or more data types (or categories). Weight, number of steps walked, number of calories burned, heart rate, etc., are each an example of such health data. Other data types (e.g., outside of health information) are also envisioned including, but not limited to, hours worked, hourly rate, miles per hour, pages read per minute, etc. A user device of the physician allows for ready selection of a set of data of health information relevant to treatment and/or diagnosis, while the user device of the patient determines a subset of the requested data set authorized by the patient to be sent to the physician.

In some embodiments, a first-party application framework may be executed on a user device of the patient that is configured to receive, store, manage, and/or provide such user information to a service provider, to third-party applications, to other first-party applications, and/or to local storage of the user device. As part of the first-party framework, a first-party process may be executed by processors of the user device. The first-party process may include, but is not limited to, a daemon or other background process configured to communicate with the third-party applications, the O/S of the user device, and/or electronic storage of the user device. In some instances, first-party process may be configured to manage a data interchange for sharing some user data with third-party applications as well as the physician. In this way, the first-party process may allow the physician to access user information that was initially provided by the third-party application, a first-party application, or other third-party applications. Since health information of a user may be considered extremely personal and/or confidential, the user is provided with the ability to protect or otherwise not share some of the heath information with the physician or certain physicians. In some examples, each third-party application may be instructed to request authorization for accessing particular (or all) data from the data interchange before transmitting the requested health information to the physician.

In some embodiments, when a physician requests a set of data from a user's health information, the first-party process may be configured to mask whether the user has granted the authorization request. In other words, the physician may not be able to identify whether the user has granted authorization or whether the user has not entered data for that data type. In some examples, this masking may be implemented by providing the same response (e.g., an empty or null result) in either case. That is, the first-party process may instead indicate to the physician application that the authorization request was provided to the user, and not indicate the user's response. Thus, if the user has not provided a data entry for the weight data type, the physician may receive a null result when attempting to retrieve that data type. Similarly, if the user has provided their weight, but has not authorized access to the physician, when the user's weight is requested, the first-party process may also provide a null or empty result (even though a data entry for that data type exists).

In other embodiments, third-party applications may be able to subscribe to certain data types, and the first-party process may be configured to automatically wake up the third-party application (e.g., in the background) and ensure that the third-party application is able to process the data as needed to transmit requested data to the physician. For example, a third-party application of the user may subscribe to a blood pressure data type and indicate an associated subscription frequency. Based at least in part on that frequency, when a new blood pressure reading is received by the first-party process, the process may wake up the appropriate third-party application background, provided with the new data and provide it with the updated data. The process may then wait for confirmation that the third-party application has processed the data. If the process does not receive the confirmation within a specified time, the process may again launch the third-party application, provide the data, and wait for confirmation. In this way, the process can ensure that the third-party application receives the data even if the user has not explicitly requested it. In this manner, the physician can receive the most recent up to date health information requested.

In some embodiments, a plug-in framework may be utilized to implement data types that are initially available for use by the first-party process and/or registered third-party applications. Plug-ins of the plug-in framework may register new data types that adhere to different identifiers so they can store their own data in the database automatically. In some examples, the plug-ins may be implemented as code that can read application programming interface (API) method calls with identifiers and/or strings associated with the data types. This may facilitate classification of types of health information to allow ready selection of requested data sets by the physician as well as allowing the patient ready authorization of data to be sent. Further, by utilizing an asset download, a service provider may enable the addition of new data types not initially provided with the first-party process (e.g., on demand). As such, the service provider may identify one or more data types not initially implemented within the first-party framework that are being requested by users/developers. The service provider may publish information about the new data type and/or how to utilize it, as well as identify whether the data type is authorized for release to a physician or medical facility upon request.

In other embodiments, the first-party process or framework or an associated first party application sets an authorization status of each field of data upon being received or accessed. The authorization status may be informed by a setting or input into the third-party application or may be set independently from the third party application. For example, a user patient may set or classify each item of information or type of data as a setting or selection made within the first-party framework of the patient device, regardless of any authorization setting made with a third-party application. This aspect facilitates improved control of patient authorizations for release of health information data to a physician, since the authorizations can be set and controlled by the patient from a central location using the first-party process itself. In another aspect, the first party process includes a prompt to the user requesting that the user set an authorization status of a field of information or type of information. This may be performed upon receipt of new information or types of information or before releasing of information after a request for the information has been made by the physician.

FIG. 1 illustrates a simplified diagram of a tele-medicine system 100 with enhanced physician-patient communication, in accordance with embodiments of the present invention. The system 100 includes a portable electronic computing device 102 (e.g. smartphone, tablet) associated with the patient through which the patient or a caretaker of the patient (e.g. parent, nurse) can initiate a tele-medicine session with the physician as well as communicate health information to a first physician, typically to an electronic user device associated with the physician (e.g. smartphone, tablet). The portable or mobile device 102 of the patient typically includes a plurality of health data elements stored on a memory of the device or on a patient data server 320 (e.g. server, cloud) accessible to the first portable computing device 102. Health information of the patient is received in the mobile device 102, either input by the patient or acquired from one or more sensor devices, such as a wearable sensor device 101 or a specialized auxiliary sensor device 103, and wirelessly transmitted to the patient data server 320. The patient data server 320 may be coupled to any number of third-party service providers 300 or regulated medical service providers 301 that may utilize the acquired health information received from the patient data server 320 and perform additional health related services, such as processing health data to determine trends or various other health metrics. Such processed data is generally made available to the mobile device 102 through the patient data server 320. The physician electronic device 402 is communicatively coupled with the physician data system 420, which includes access to the electronic medical record (EMR). The physician data system 420 may also be coupled to one or more regulated medical service providers 301 and the patient data server 320. In this system, the mobile device 102 of the patient and the physician device 402 are communicatively coupled through the patient server 320 and physician data system 420 such that the tele-medicine session can be conducted remotely without requiring the patient to visit the clinic and allow rapid transmission of targeted relevant data needed for the session, while also safeguarding patient privacy.

In one aspect, mobile devices 102 in combination with the one or more sensor devices, in this example, wearable device 101 and/or auxiliary sensor device 103, that allow collection and/or analysis of large amounts of health data, typically far greater amounts than conventional medical visits entail. Dealing with such large amounts of data, however, may negate any associated benefits such information provides as it may prove difficult and overly time consuming to manage using conventional methods. The above described system provides a method of dealing with requesting of relevant data from vast amounts of data in a rapid and manageable manner and facilitate submission of the requested data to the physician while still safeguarding patient privacy, thereby improving efficiency and feasibility of using such large amounts of data in treatment and diagnostics. For example, the system allows the physician to rapidly select data desired for a treatment session, such as through pre-selection or categorical selections, from a large volume of data potentially available, and further allows the patient to rapidly and selectively authorize the release of a subset of data requested by the physician. Upon initiation of a tele-medicine session with a mobile device 102 communicating with the physician device 402 through the patient data server 320 and physician data system 420, the physician requests a set of data associated with the condition for which treatment or diagnosis is being sought by the patient. In response to the medical information request received from the physician, the mobile device 102 identifies a subset of data from the set of data being request that is authorized by the patient for release. The identification of data may be determined by the mobile device according to a default or pre-selection by the patient. This selection can be simplified by grouping data according to categories or types of data and allowing the patient to select authorizations according to the category or type, as shown for example in FIG. 10B.

In some embodiments, the health information may be input directly into the mobile device 102 by the patient or may be obtained through one or more health information acquisition devices or sensors, such as wearable device 101 (e.g. watch, wristband) that the patient wears such that one or more sensors of the wearable device measure one or more parameters that can be used to determine health data, either directly or indirectly. For example, the wearable device 101 may measure body temperature directly or may measure activity levels by use of one or more accelerators. In some embodiments, the wearable device 101 is incorporated within the first-party framework of the mobile device 102. The one or more sensor devices may be specialized for sensing and/or measuring various health metrics, including but not limited to activity level, activity tracking, respiration, body temperature, heart wellness data, hydration levels, perspiration, blood glucose, salinity, sleep cycles, posture, $O_2$ levels, muscle engagement, or any combination thereof. The collected data may or may not be specific to the condition being treated and/or diagnose and may be collected without requiring any additional input from the patient to initiate collection of the sensed data. In some embodiments, the sensed data is collected over a duration of time, the duration generally exceeding a few days, such one or more weeks, months or years. Typically, these auxiliary health sensor devices 103 are third-party devices that are supported by a third-party application and managed by used of a third-party service provider 300. Such sensors 103 may also be a regulated medical device that is supported through a regulated medical service provider 301. The mobile device 102 communicates the health information to the patient data server 320, which may be selectively accessed by the physician data system based on identification of a subset of data authorized by the patient to be released by the physician.

Figure 2:
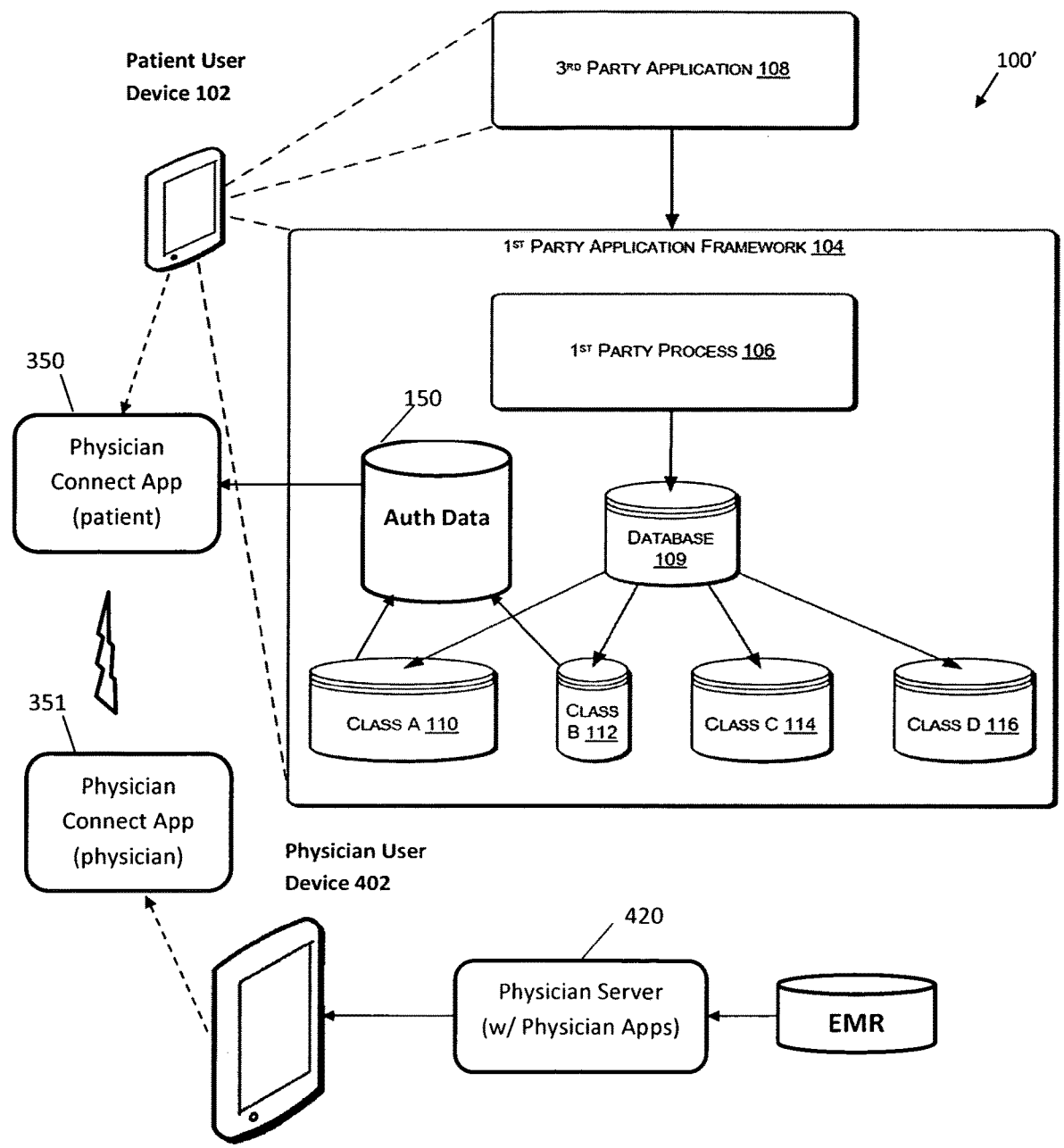
FIG. 2 is a simplified block diagram illustrating an example system architecture for managing user information as described herein, in accordance with certain embodiments.

FIG. 2 illustrates a simplified architecture diagram 100' depicting a patient device 102 configured to implement a first-party application framework 104 and managing exchange of health information (e.g. the plurality of health data elements) received by the mobile device 102. As noted above, the first-party application framework 104 may be configured as an application framework for managing user data of a plurality of data collection devices. While health data is used as an example throughout much of this disclosure, any type of data that may be collected or otherwise provided about a user may be managed by the first-party application framework 104. In some examples, because the first-party application framework 104 is provided or otherwise controlled by developers of the user device 102 and/or its associated O/S, the first-party application framework 104 may be considered a trusted framework with full access to all user data. In some examples, the first-party application framework 104 may be configured with one or more processes executed by the user device 102. For example, a first-party process 106 may be executed in the background such that the user is not aware that it is running. In this way, the first-party application framework 104 may be able to manage the user data whenever desired without interfering with the everyday use of the user device 102. Additionally, in this way, the first-party application framework 104 may be able to communicate with one or more third-party applications 108 to allow for rapid transmission of the requested data to the physician.

In some examples, the first-party process 106 may be configured to manage (e.g., store, retrieve, encrypt, etc.) user data via a database 109 of the user device 102. As part of the first-party application framework 104, the database 109 may be divided or otherwise logically separated into a plurality of classes of data stores. For example, the user data may be stored in at least one of a class A data store 110, a class B data store 112, a class C data store 114, and/or a class D data store. In some examples, the class A data store 110 may be configured to store personally identifiable user information (e.g., personal health, fitness, or activity data). In some examples, this data is only available to the third-party application 108 when the user device 102 is unlocked. By way of example, the user device 102 may be unlocked when the user associated with the user device 102 has correctly entered his or her user identifier (ID) and password (e.g., when logging in and/or unlocking the lock screen). Class B data store 112 may be configured to store "journal" type data. Journal data may include, but is not limited to, personally identifiable user information and/or other metrics associated with use of one or more data collection devices and/or the third-party application 108. When the user device 102 is locked, the journal data of the class B data store 112 may be inaccessible to the third-party application 108. However, in some examples, data from a data collection device or an application (e.g., the third-party application 108) may be read from or written to the class B data store 112 by the first-party process 106 while the device is locked as long as the first-party process 106 is active. If, however, the first-party process 106 fails or otherwise becomes inactive in the process of reading or writing data to the class B data store 112, the data may become permanently inaccessible, and new data may not be written to the class B data store 112 until the first-party process 106 and/or a new session of the third-party application 108 have relaunched. In this way, the data of the class B data store remains securely accessible because it is only accessible to the first-party process 106 while receiving data from a third-party application 108 during the active session, and no other applications can read that data.

In some aspects, the class C data store 114 may be configured to store metadata associated with the management of the user health, fitness, and/or activity data. This metadata, in some cases, may only be accessible after the first unlock of the user device 102. As such, if the user device 102 reboots (based at least in part on a software issue or a loss of battery power), this data may not be available until the user unlocks at least once. In some aspects, this may prevent jailbreaking or other hacking techniques from accessing this data. The metadata stored in the class C data store 114 may include subscription information, access permission information, and/or safe metadata, but may not, in some examples, identify or be directly associated with any health information (e.g., the data stored in the class A data store 110). The class D data store 116 may be configured to store free-form (e.g., unstructured) information provided by the user. In some examples, this may be health data; however, it may not be updatable and/or linked to any third-party applications (e.g., the third-party application 108) or data collection devices. The class D data may always be available to the first-party process 106 and/or the third-party application 108. In some aspects, the class D data may be pre-filled using information from the third-party application 108 and/or one or more other applications or processes. However, the user may be able to enter additional data, update the data, include incorrect data, or otherwise configure the information in the class D data store 116 as they see fit. The class D data may be available on the lock screen of the user device 102 without anyone (e.g., the user) logging in or otherwise unlocking the user device 102. In this way, the lock screen or another accessible screen of the user device 102 may be analogous to a medical ID bracelet. In some cases, an emergency icon or other function on the lock screen may enable the presentation or rendering of the class D data upon request for anyone (e.g., an emergency medical technician or the like) to see. Further, in some aspects, the third-party application 108 may not have access to the class D data, in part because it may be unstructured data that would be difficult for the third-party application 108 to process.

In one aspect, the first-party application framework 103 identifies health information data authorized by the patient to be sent to the physician as Authorized Data 150. Such an identification may be based on a default, a pre-selection or a live input from the patient in response to a query. Typically, the most common types of information being requested and identified as Authorized Data would be Class A and Class B types of information. Some embodiments may include release of various other types of data, for example to allow further processing of collected data by an application on the physician device. While Authorized Data 150 is shown schematically as a separate element, it is appreciated that such authorized data is not required to be stored in a separate location, nor is it required to be identified before the request for information is made. This may instead be accomplished in various different ways, for example, by tagging or using a specific identifier for each field of data to denote which data items are authorized for release by the patient and to which parties the data is authorized for release. In some embodiments, the identification of authorized data is determined only after receiving a request for data. In systems having exceedingly large amounts of health information data, this approach may be more efficient, since the data is only analyzed to determine authorization of the data set that is being requested. Since a physician has limited time and resources to review health information for each patient, the amount of health information would generally be limited and targeted to factors most relevant for that patient and/or the condition being treated or diagnosed. In some examples, the requested info is narrowed or targeted such that the returned information is displayed on the user interface of the physician device at one time to allow for easy comparison and viewing by the physician, such as shown in FIG. 12C.

As shown in FIG. 2, communication of data between the patient mobile device 102 and the physician device 402 may be facilitated by use of an application common to both devices, such as the Physician Connect Application 350, 351 provided on the patient device 102 and the physician device 402, respectively, such as shown in System 100' of FIG. 2. In this aspect, the devices may communication through a common server (e.g. physical server or cloud) that supports the common application, as opposed to going through separate but interconnected server information. The physician device may separately couple with the physician server 420 as well as the EMR to import additional information external to the health information data associated with the mobile patient device 102. While the application may be common to both devices, generally, the application would include features suited for the particular uses associated with each device. For example, the application may display health information data more succinctly on the patient device, than on the physician device. In addition, the application of the patient device requires a feature that allows the patient to select data authorizations, while the physician device application requires a feature that allows the physician to select sets of data to be requested. In some embodiments, this application is a first-party application on each of the devices and may be incorporated partly or fully into the first-party framework. For example, the application may run in the background during normal operation of either device, so as to be readily responsive to a communication from either device using the application. By using a first-party application or platform for facilitating session initiation and communication regarding physician health information request and release of authorized data by the patient, the system allows a central location from which the patient can manage and authorize release of data that may be provided by various different sources (e.g. third-party application, third-party servers). While these different sources and third-party applications/servers may each include their own permission and authorizations regarding storage and transmittal of secure health information data, routing the transfer of data through the first-party application ensures that the patient is aware exactly what data is being released and allows the patient an opportunity to change authorizations of data and release data, regardless of permissions associated with the third-party application or other data source.

Figure 3:
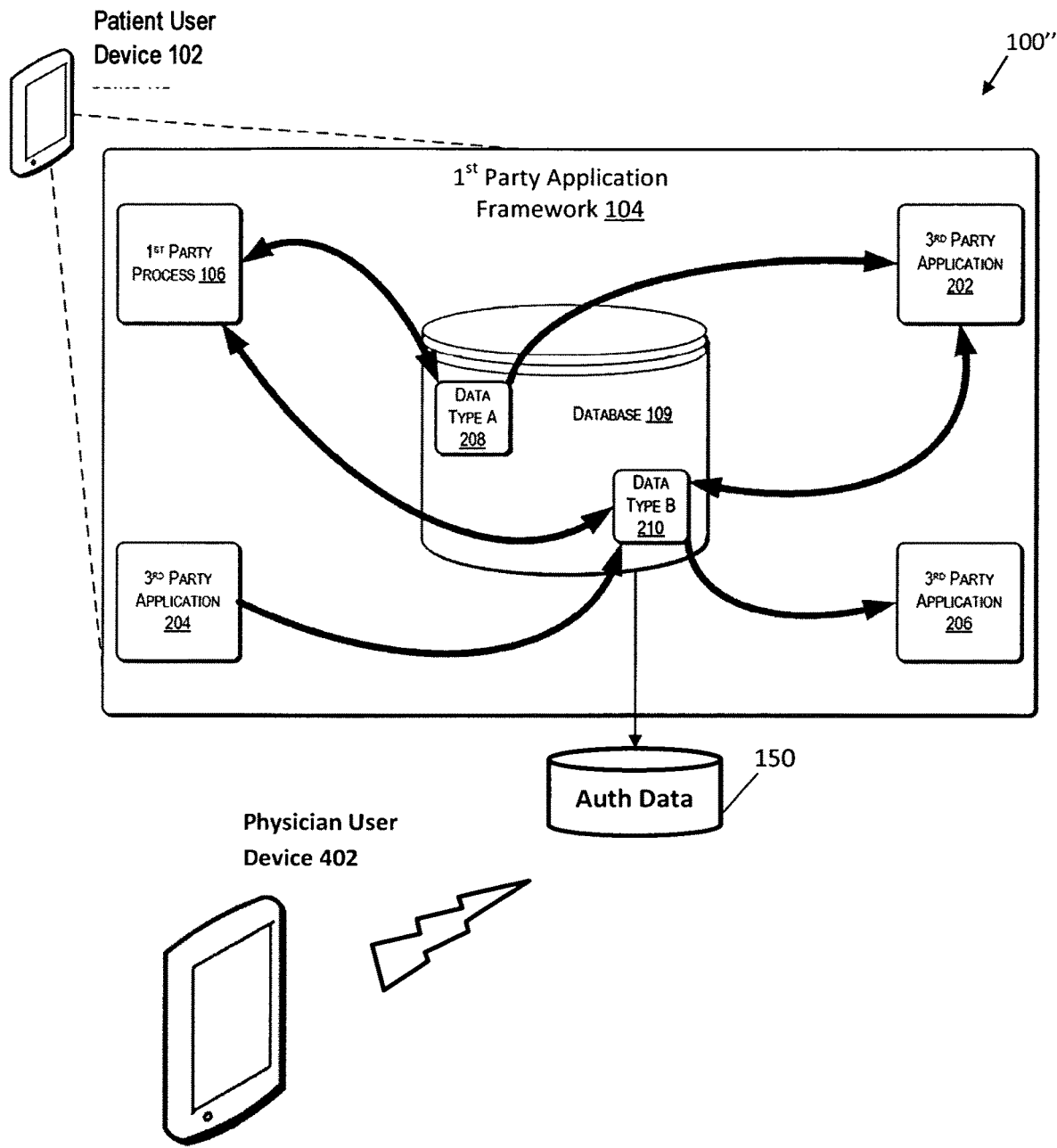
FIG. 3 is another simplified block diagram illustrating another example architecture for managing user information as described herein, in accordance with certain embodiments.

FIG. 3 illustrates a simplified architecture diagram associated with another system 100" that depicts additional implementation details associated with the first-party application framework 104 and how user data stored in the database 109 can be accessed by the first-party process 106 and/or one or more different third-party applications 202, 204, 206 (e.g., the third-party application 108). In some examples, as noted above, the database 109 may allow the first-party process 106 and/or the third-party applications 202, 204, 206 to write health and medical data into the database 109 and read it back out. In various aspects, the third-party applications 202, 204, 206 may actually populate the database 109 with data more than the first-party process 106. Thus, the first-party application framework 104 may be configured to act as a data interchange between the applications as well as to the physician.

In some embodiments, the portable device of the patient or an associated framework is configured to identify whether health data stored on or accessible with the device is authorized to release to a health care provider. Such identification may made upon receiving or storing of the data, or may be made at later time, such as after receiving a request for a set of health data that includes the given data. The identification may be broadly applied to all health care providers, or may be adapted for a class of providers or for a given application. For example, one such item of information that a user may desire not be included in released health information is an activity level. An activity level may be a metric provided by a first party process or application or a third party application. The patient user may set the activity level as private such that it is available only to the associated first party process/application or third party application, and is not released in response to any health information request. In another aspect, the identification of patient authorized data may be variable or conditional based on one or more factors, such as a specialty or sub-specialty of the physician, the condition for diagnosis or treatment for which the session was initiated, an affiliation of the physician or medical personal, and the like. For example, a user patient may desire that an activity level be released only to their primary physician, if requested, and withheld from any information request from any other physician. Alternatively, the user may authorize release of specific data and indicate exceptions, for example a user patient may desire that the activity level be released in response to any physician request for that data with the exception of any physician in a dermatological specialty. In another aspect, an item of data received by the patient's device may have a default unless authorization is changed by the patient, for example a default may be to disclose an item of information if requested by the physician unless indicated otherwise by the patient during pre-selection or confirmation before sending to the physician. In another aspect, the default value may vary according to a type of data or according to a type of information that is commonly maintained as private or confidential. For example, certain types or classes of drugs may automatically default to not being disclosed if requested, unless the device receives patient input to change the default.

As noted above, the user device 102 may be configured to manage a data interchange for reading and/or writing user data to the database 109, and for sharing that user data among one or more authorized third-party applications. In some examples, the data collection device 302 may be configured to provide health, fitness, activity, and/or medical data of the user to a third- or first-party application (or process). In turn, this data may be shared, aggregated, and/or accessed via the first-party framework module 104 that may be configured to implement the first-party application framework 104 of FIGS. 2-3. The user device 102 may be any type of computing device such as, but not limited to, a mobile phone, a smartphone, a personal digital assistant (PDA), a personal computer (e.g., laptop or desktop), a thin-client device, a tablet computer, an electronic book (e-book) reader, a wearable device, etc. In some examples, the patient device 102 may be in communication with the service provider computers 304 and/or the data collection device via the networks shown or via other network connections.

In one illustrative configuration, the user device 102 may include at least one memory and one or more processing units (or processor(s)). The processor(s) may be implemented as appropriate in hardware, software (e.g., computer-executable instructions, firmware, etc.), or combinations thereof. Computer-executable instruction or firmware implementations of the processor(s) may include machine-executable instructions written in any suitable programming language to perform the various functions described. The user device 102 may also include geo-location devices (e.g., a global positioning system (GPS) device or the like) for providing and/or recording geographic location information associated with the user device 102. The memory may store program instructions that are loadable and executable on the processor(s), as well as data generated during the execution of these programs. Depending on the configuration and type of user device 102, the memory may be volatile (e.g., random access memory (RAM)) and/or non-volatile (e.g., read-only memory (ROM), flash memory, etc.). The user device 102 may also include additional removable storage and/or non-removable storage including, but not limited to, magnetic storage, optical disks, etc. The disk drives and their associated non-transitory computer-readable media may provide non-volatile storage of computer-readable instructions, program modules, data structures, and other data for the computing devices. In some implementations, the memory may include multiple different types of memory, such as RAM, static random access memory (SRAM), dynamic random access memory (DRAM), or ROM. While the volatile memory described herein may be referred to as RAM, any volatile memory (e.g., that does not maintain data stored therein once unplugged from a host and/or power) would be appropriate.

Additional types of computer storage media that may be present in the user device 102 may include, but are not limited to, phase-change RAM (PRAM), SRAM, electrically erasable programmable read-only memory (EEPROM), flash memory, compact disc read-only memory (CD-ROM), digital video disc (DVD), magnetic cassettes or tape, magnetic disk storage, or any other medium that can be used to store the desired information and that can be accessed by the user device 102. Combinations of any of the above should also be included within the scope of non-transitory computer-readable media. Alternatively, computer-readable communication media may include computer-readable instructions, program modules, or other data transmitted within a data signal, such as a carrier wave, or other transmission. However, as used herein, computer-readable storage media does not include computer-readable communication media. The user device 102 may also contain communications connection(s) that allow the user device 102 to communicate with a data store (e.g., the database 109), or another computing device via one or more networks. The user device 102 may also include I/O device (s), such as a keyboard, a mouse, a pen, a voice input device, a touch input device, a display, speakers, etc.

Turning to the contents of the memory in more detail, the memory may include an operating system and/or one or more application programs or services for implementing the features disclosed herein including an authorization module 334, a background module, an extension module, and/or an aggregation module 340. In some examples, the authorization module may be configured to manage authorization requests from third-party applications for access of user data stored in the database 109 (e.g., class A data of FIG. 2). The authorization module may also be configured to mask when a user denies authorization to a third-party application for a particular data type. In this way, the third-party application may not be able to infer anything about the user based at least in part on the denial. The background module 336 may be configured to launch and/or relaunch third-party applications in as background process. In some examples, the background module 336 may also be configured to verify that the third-party application has finished processing the data it requested, by continuing to relaunch the third-party application in the background until notification is received that the third-party application has completed processing. The extension module 338 may be configured to handle registering new data types with the first-party framework module in order to extend the functionality of the first-party application framework 104 of the systems shown in FIG. 2 or FIG. 3. Further, the aggregation module may be configured to aggregate or otherwise combine (and, in some examples, provide presentation for) user data received from multiple different data sources. The service provider computers may also be any type of computing device such as, but not limited to, a mobile phone, a smartphone, a PDA, a personal computer, a thin-client device, a tablet computer, an e-book reader, a wearable device, etc. In some examples, the service provider computers 304 may be in communication with the user device 102 and/or the data collection device 302 via one or more networks or via other network connections.

In some embodiments, including those shown in FIGS. 2 and 3, the patient user device 102 and physician user device 402 communicate directly with each other, such as through near field communication. It is appreciated that at least some of the information transmitted by either device may be accessed by the respective device through one or more networks associated with the device, or first-party applications or third-party applications. In some embodiments, the devices communicate with each other through an NFC module integrated within each device, using short-range RF module technology to transmit the health information request to the patient and to transmit the authorized subset of data in response. This may be performed while the patient and physician are in close proximity, such as in an examination room of a clinic. Such systems illustrate the above noted advantages in efficiency over conventional methods by utilizing the same methods described herein even when the physician and patient are in close proximity. For example, in conventional approaches, the patient may be required to fill out a form with health information which is then entered by medical personnel or the physician into the physician system, or the patient may be subjected to a lengthy interview with various medical questions before examination commences. The system circumvents these inefficiencies and redundancies by allowing the physician to rapidly request health information from the patient and allowing the patient to rapidly submit an authorized subset of data within a few minutes or less, without requiring any interview or forms. Moreover, the amount of information has the potential to be much larger and comprehensive than the limited information obtained from forms and standard interviews used in conventional methods.

Figure 4:
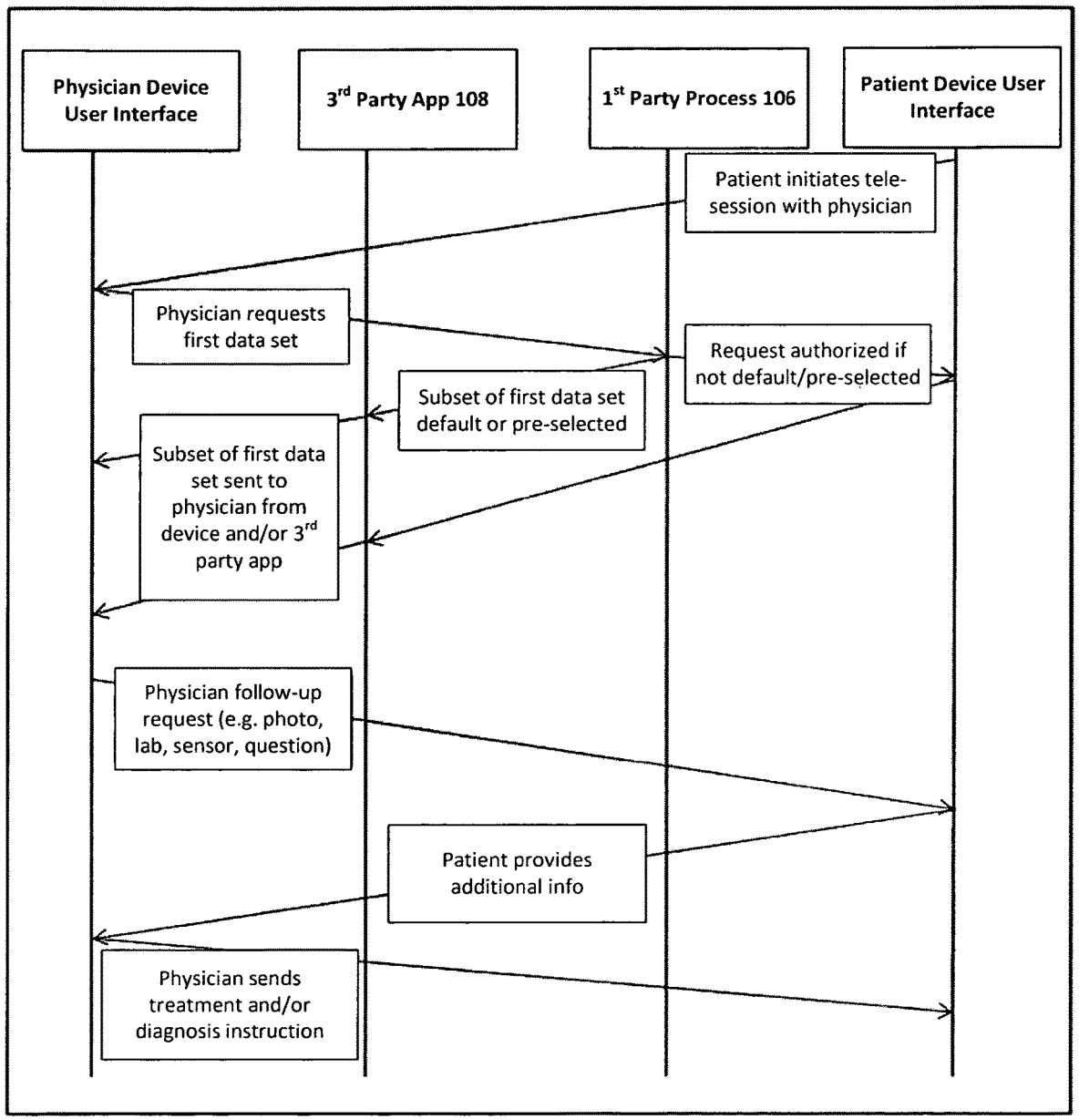
FIG. 4 is a sequence diagram illustrating additional features of managing user information between patient and physician, in accordance with certain embodiments.

FIG. 4 illustrates an example sequence diagram describing features of the management of health information during a tele-medicine session conducted using a system in accordance with the invention. In one aspect, at least some of the health information may be stored on a third-party server associated with a third party application or securely stored on the patient device and securely associated with the third-party application. In such cases, a first-party process or framework may need to manage the appropriate sequence of authorizations to obtain the requested information from the third-party applications. In the example shown in FIG. 4, a patient initiates a tele-medicine session with a physician using a user interface of the patient device (see for example FIG. 10A). The tele-medicine session may be initiated by the patient to diagnose and/or treat a particular condition of the patient or may be a follow-up to an earlier session. The physician is notified of the session via a user interface of a physician device, with which the physician requests a first data set of health information to facilitate treating and/or diagnosis of the patient. In some embodiments, if identification of authorized patient data has already been made, such as through the use of default or pre-selected authorizations, the patient device may automatically determine a first subset of the requested set of data that is authorized to be sent. In some embodiments, this may be performed without requiring additional input from the patient, although typically, the patient device will prompt the patient to confirm the authorizations and release of the first subset to the physician. If the authorized data from the requested data has not already been identified, then the patient devices present an authorization prompt to the patient via a user interface of the patient device. This prompt allows the patient to select, either individually or categorically by type or group of information, the information authorized to be released. Once the first subset of authorized data is selected, it is sent to the physician, which may further include obtaining any required data from a third-party application.

In some embodiments, the physician may communicate a follow-up request for additional information (e.g. photos, laboratory results, sensor results, additional questions). For example, based on the health information received, the physician may wish to conduct a verbal interview of the patient using the respective device or to obtain a photo or video of the patient, for example a photo of a rash or burn. In return, the patient may use the system to provide the additional information requested, after which the physician may send treatment and/or diagnosis instructions.

FIG. 5 illustrates an example table 500 of values for demonstrating sample pre-determined authorizations for types of information provided to a physician by the first-party process 106 of FIG. 1, for different scenarios. For example, in the table 500, the first column represents data type 502, the second column represents values 504 for that data type received from a third-party application (or entered by a user), the next column represents authorization 506, the fourth column represents whether the data was requested 508 by the physician, and the final column represents an example result that would be provided to the requesting third-party application 510 based at least in part on the values of the other columns, per row. As can be seen from FIG. 5, a subset of data may either omit the data entirely if not authorized or conditionally authorize release of specific data to certain physicians. In one non-limiting example, row 512 may represent a scenario for the "heart rate" data type. In this example, the user's heart rate may have been recorded as 78 beats per minute and any physician requesting heart rate data will receive the data since the user has pre-approved the authorization request. In contrast, the "weight" data type is pre-authorized only for release to physician X such that the data would be omitted in the subset transmitted to any other physician requesting weight. Certain conditions if not authorized, such as the data type "HIV" 520 are not released when requested by any physician. It should be noted that the result returned for a data type that is not authorized to be released is the same as if there was no data of that type. Thus, the result returned for data that is not authorized is not suggestive to a physician that only a subset of data has been returned or that there may be data for some types of data that were not returned. In this way, the denial and approval of authorization requests can be masked by the type of response given to the requesting application. In another aspect, the authorizations may include truncating or modifying the data to include less specific data that what resides in the mobile device 102. For example, a pre-authorization of a health information for glucose 514 may be to report the actual value only to Physician X, and to report only a range (low, normal, high) to any other physician (e.g. Physician Y) that requested glucose data. In another aspect, the pre-selection may be to prompt the patient each time the data is requested, such as is the case for information of an activity level 522.

Figure 6:
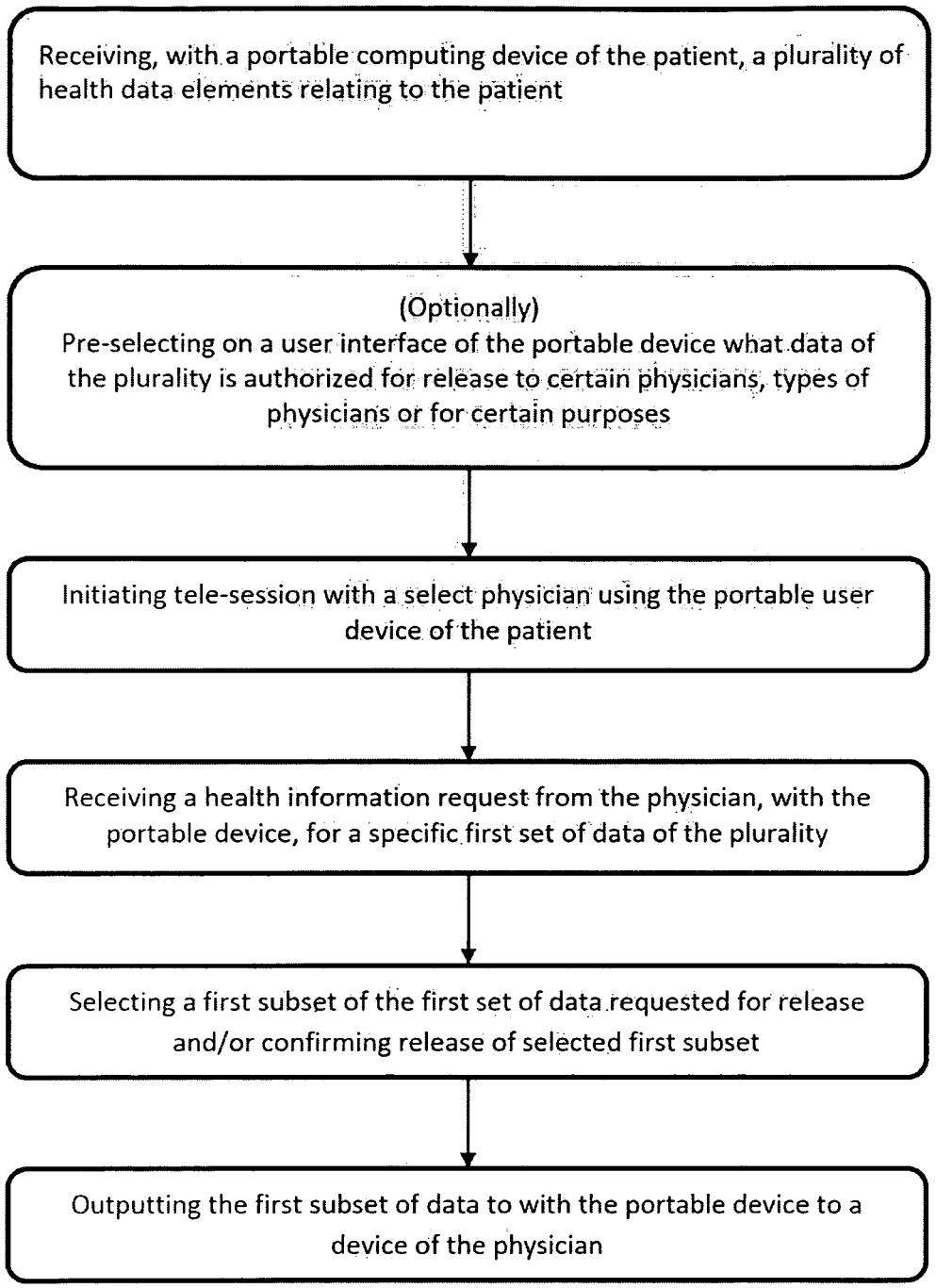
FIG. 6 is a flowchart of a method for managing patient information, in accordance with certain embodiments.
Figure 7:
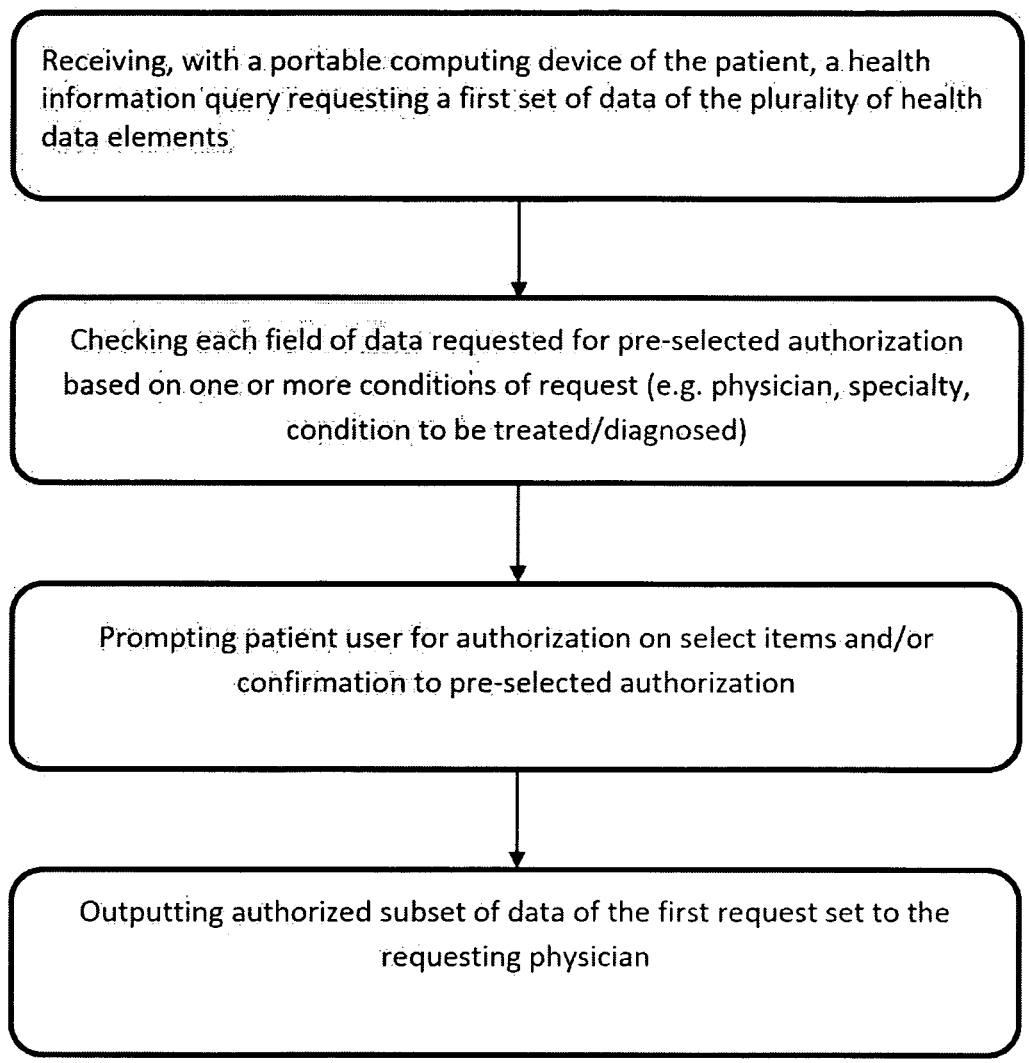
FIG. 7 is a flowchart of a method for managing user information as described herein, in accordance with certain embodiments.

FIGS. 6 and 7 illustrate example flow diagrams showing processes for managing authorization of information requested from a physician by a patient using the system described herein. The method of FIG. 6 includes steps of: receiving, with a portable electronic device of the patient, health information of the patient that includes a plurality of data; optionally, pre-selecting on a user interface of the portable device what data of the plurality is authorized for release to certain physicians, types of physicians or for certain purposes; initiating a tele-session with a select physician using the user device of the patient; receiving a health information request from the physician, with the portable device, for a specific first set of data of the plurality; selecting a first subset of the first set of data requested for release and/or confirming release of selected first subset; and outputting the first subset of data to with the portable device to a device of the physician. The method of FIG. 7 includes steps of: receiving, with a portable device of patient, a health information request for set of data from plurality of data; receiving, with a portable device of patient, a health information request for set of data from plurality of data; checking each field of data requested for pre-selected authorization based on one or more conditions of request (e.g. physician, specialty, condition to be treated/diagnosed); prompting patient user for authorization on select items and/or confirmation to pre-selected authorization; and outputting authorized subset of data of the first request set to the requesting physician.

Figure 8:
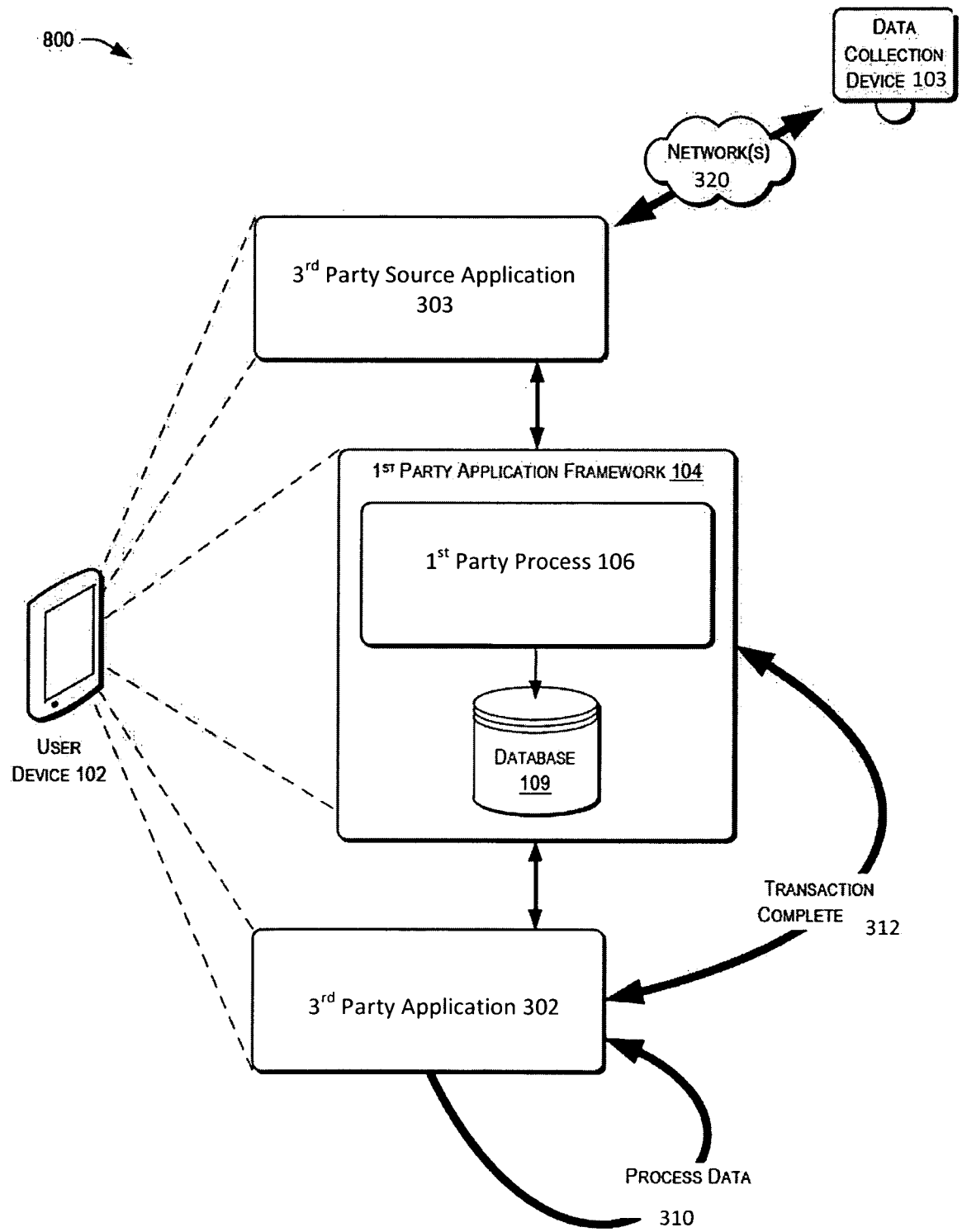
FIG. 8 is a simplified block diagram illustrating another example architecture for managing user information, in accordance with certain embodiments.

FIG. 8 illustrates another example system 800 using a patient device 102 and associated health information collection scheme in accordance with the present invention. FIG. 8 depicts a patient device 102, the first-party application framework 104, and the first-party process 106 of FIG. 2. In some examples, one or more third party applications (e.g., third-party source application 802 and/or third-party application 804) may be in communication with the first-party application framework 104 and/or the first-party process 106 for providing user information collected by a health data collection device 101. In some examples, the data collection device 103 may be any wearable or specialized mobile device configured to collect activity, health, medical, and/or fitness information about a user. This information may then be provided to one of the third-party applications (e.g., the third-party source application 303 in this example) via one or more networks. Once received by the third-party source application 303, the information can be provided to the first-party process 106 for storage in the database 109.

In at least one non-limiting example, the third-party application 303 may be configured to subscribe to one or more data types of the user information stored within the database 109. For example, the third-party application 804 may subscribe to the "weight" data type with a frequency of "daily," and also subscribe to the "blood glucose level" data type with a frequency of "immediate." As such, in some examples, the first-party process 106 may launch the third-party application 804 in the background when certain actions occur based at least in part on the subscription. For example, whenever the third-party source application 303 provides a new blood glucose reading (assuming the data collection device 103 collects and provides such data), the first-party process 106 may automatically launch the third-party application 804 and enable it to request the new reading. In this scenario, the third-party application 303 was launched nearly immediately (e.g., within a second or so) after the new blood glucose reading was received because the subscription frequency was set to "immediate." Alternatively, if the new reading had been weight; the third-party application 804 may not been launched until the end of day based at least in part on that subscription being set to "daily." In some embodiments, upon receiving a request from a physician for a set of data, the system may acquire updates as to the each field of data, including those from third-party device associated with third-party applications, even if such devices are not scheduled to report measurements. In another aspect, the system reports the subset of data with whatever health information is stored and does not otherwise the manner in which the health information is obtained from a first-party wearable devices 101 or a third-party sensor device 103.

Figure 9:
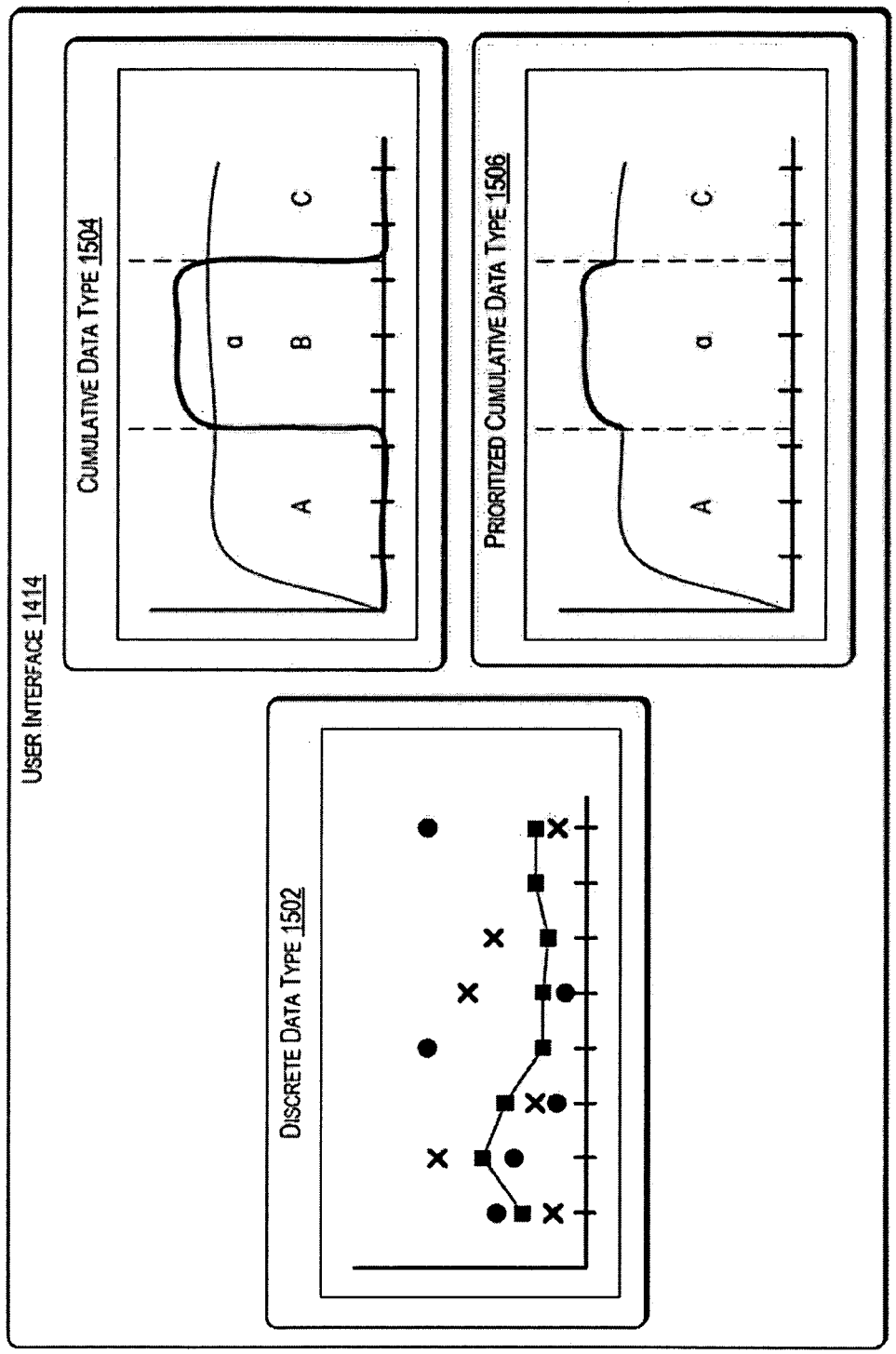
FIG. 9 is a user interface of a portable electronic device illustrating health information processed by third-party applications, in accordance with certain embodiments.

FIG. 9 illustrates an example user interface 1414 illustrating different types of data as processed by third-party applications. For example, for discrete data type presentations 1502, the UI 1414 may be configured to represent each data entry as a data point on a time graph. As shown, for the discrete data type presentation 1502, there may be multiple data entries for each segment of the total time period. For example, a user may have three different devices collecting their weight over the course of a day, week, month, etc. At each segment, the discrete data type presentation 1502 may include each data entry received by the first-party process 106 from the three different sources. Since weight is not a data type that would be added up over time (e.g., it is discrete), it may be appropriate to present each different data point for each segment. In some examples, a prioritized source may be identified by a line or other interface object/element that highlights the data points from that source.

Here, the line connecting the square points on the presentation 1502 is one example of a way to represent priority or a preferred data source.

In some embodiments, when the health data acquired is cumulative, the data may be summed or otherwise added up over the entire time period. As shown in the cumulative data type presentation 1504, this may cause a double counting problem when multiple sources provide data for the same time segments. For example, over the first third of the time period, the first-party process 106 may only have received data from a first source (e.g., A number of steps). For a cumulative data type (e.g., steps walked), the data entries at each segment may be added together to get a total. Similarly, at the last third of the time period, the first-party process 106 may also have only received data from the first source (e.g., C number of steps). However, if two sources provided step data during the middle third of the time period, adding both B number of steps and alpha number of steps would not provide an accurate total step count because the number of steps during that time period would be double counted or at least counted from two different sources. As such, using the priority information collected from the user, the UI 1414 may be able to present a piecemeal representation such as the prioritized cumulative data type presentation 1506. In this presentation 1506, the alpha number of steps may have been identified as the user's prioritized data source for this subset of the time period. As such, only alpha number of steps (e.g., coming from one source) is shown during that subset of the time period, while A and C number of steps (e.g., coming from a different source). The total number of steps aggregated over the time period in this presentation 1506 may be A+alpha+C, as opposed to A+B+alpha+C from the cumulative data type presentation 1504. In some systems, the physician may desire particular types of data or processed data, such discrete, cumulative, or prioritized cumulative, or averaged data. Depending on what applications are provided on the patient device 102, the patient device may transmit processed data in response to a health information request from the physician.

Figure 10A:
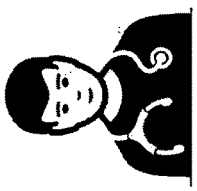
Figure 10C:
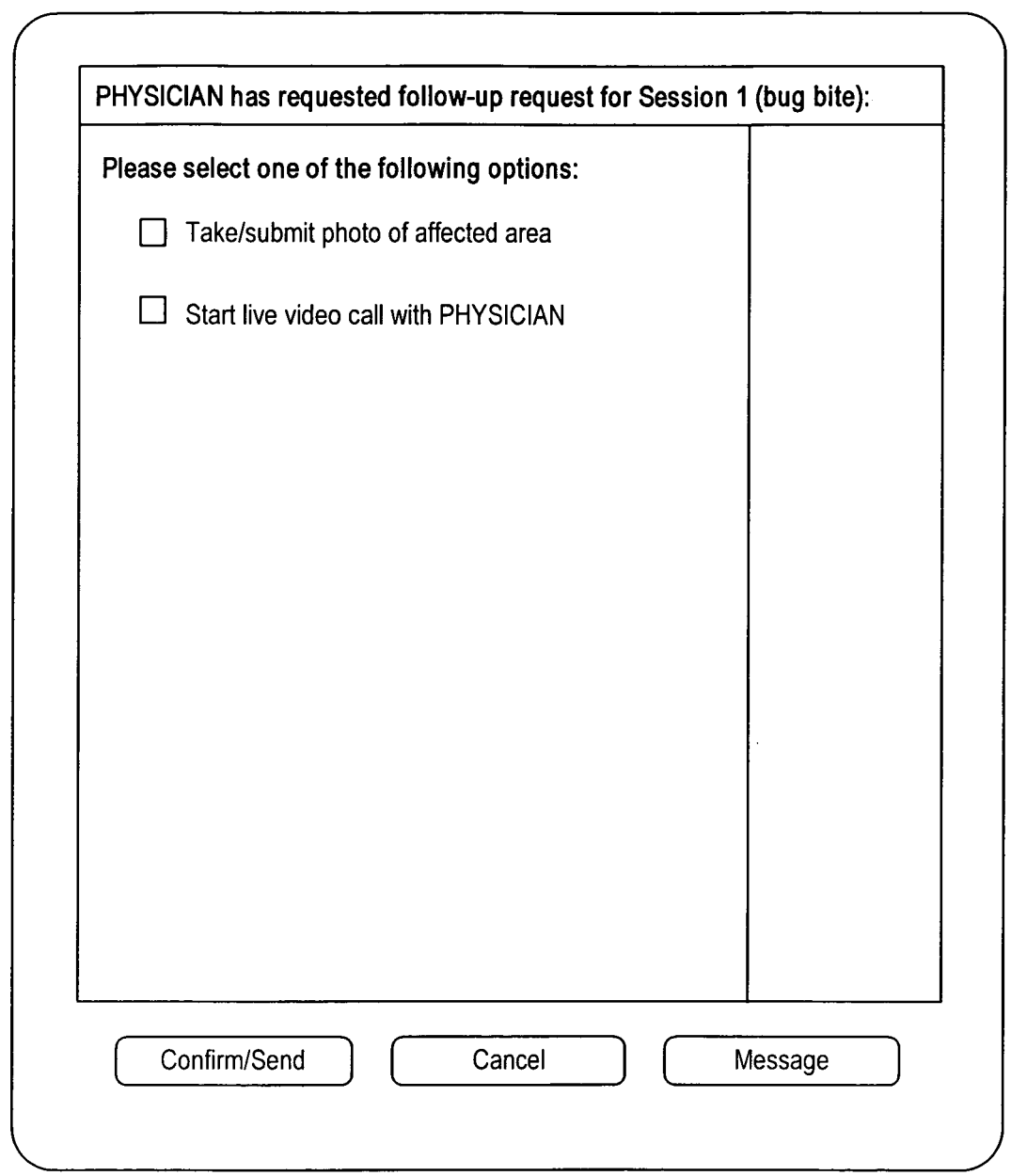

FIGS. 10A-10D illustrate a patient device 102 and associated user interface during a tele-medicine session in accordance with methods of the present invention. FIG. 10A illustrates an option screen on the user interface of the patient device 102 from which a patient may select a doctor for initiating a tele-medicine session with for treatment and/or diagnosis of a condition. In this example, the patient is seeking diagnosis/treatment for a bug bite. Depending on the patient's condition, the patient may select the physician by name or by specialty or sub-specialty, such as shown in FIG. 10A. The patient may review pertinent details of the physician, such as the co-pay, primary practice, languages spoken, education and years of experience, when selecting the physician. The patient may also choose the means of communication, for example by selecting "Talk Now" to speak with the physician or "Message" to send a text communication.

After the patient initiates the tele-medicine session and communicates their concerns or their condition to the physician, the physician sends a health information request to the patient for a set of data of the plurality of health data elements stored or accessed by the patient device. Since only a subset of the data set may be authorized by the patient, the system identifies what data of the set request is authorized to be released. In the example of FIG. 10B, the patient receives the list of requested data on the user interface of the patient device 102, on which the patient may select individually or by category what data is authorized to be released to the physician. In some embodiments, the patient device 102 may include one or more pre-sets that automatically authorize certain data to be released. For example, as shown in FIG. 10B, the patient may choose from various preset authorization options: including "Select all;" "Sensor Data;" a customized preset, "Option 1;" a category based on the specialty or practice of the physician, "General;" a preset for a particular physician or condition of the patient, or an "Anonymous" option, which automatically deselects "name/age/sex/insurance" to allow the patient to remain anonymous.

Figure 10D:
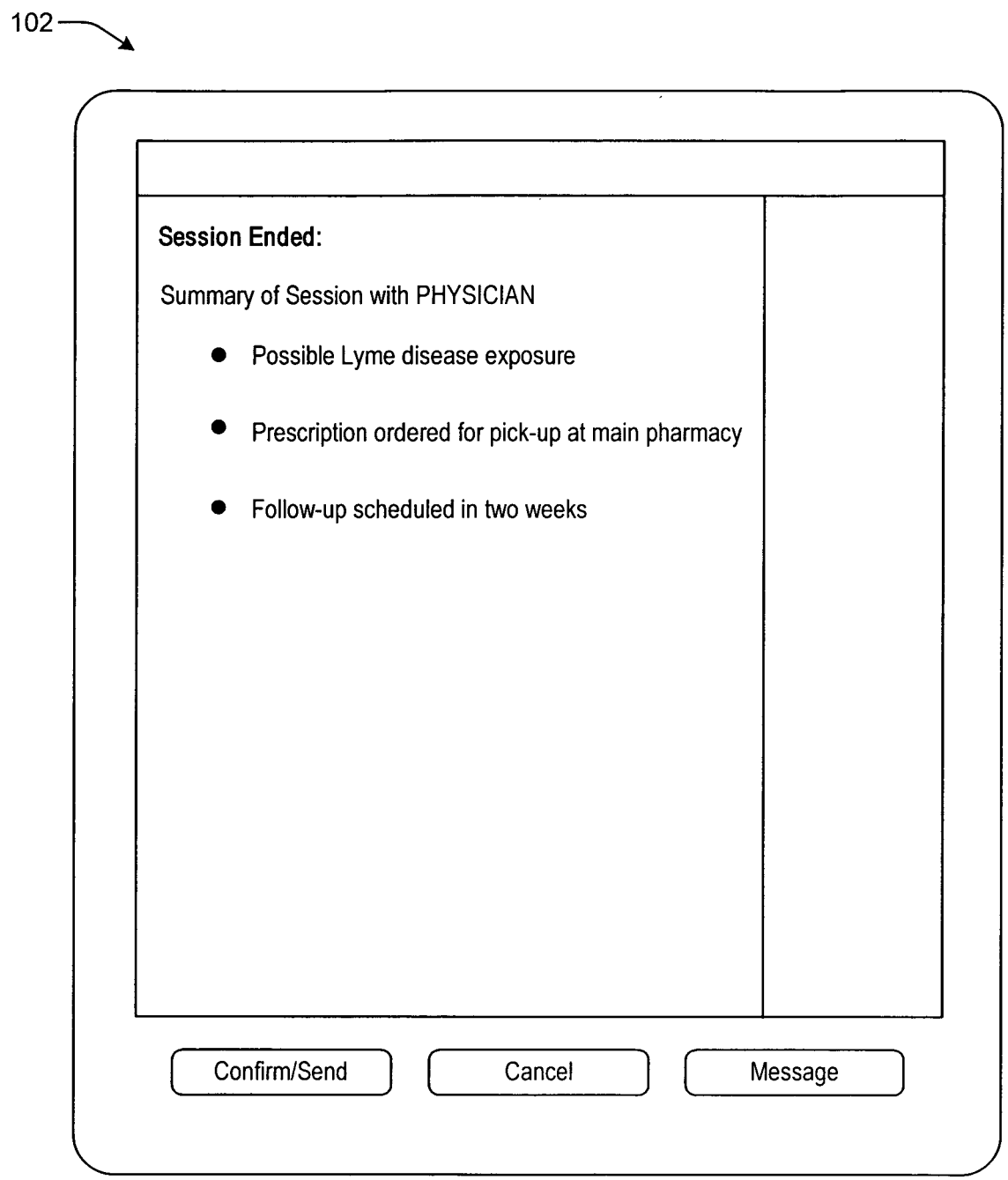

Once the authorized data has been selected or determined, the patient hits "Confirm/Send" to automatically send the subset of authorized data to the physician so as to facilitate treatment and/or diagnosis of the patient's condition. Once the physician reviews the authorized subset of data, the physician may have a follow-up request. For example, the physician may wish to speak with and/or view the patient. The physician may send a communication facilitating the follow-up, such as a communication through the patient device 102 that presents the patient with options to "take/submit photo of affected area" or to initiate a live video transmission with the physician. After the physician obtains the follow-up information, the physician may provide further instructions to the patient regarding the outcome of the diagnosis/treatment. For example, from the photo, the physician may suspect possible exposure to Lyme disease and prescribe the patient a course of antibiotics in accordance with standard practice and scheduling of a follow-up session (e.g. a tele-session or in-person session). As shown in FIG. 10D, the diagnosis/treatment instruction can be provided to the patient and summarized and additional information provided regarding follow-up visits.

Figure 11:
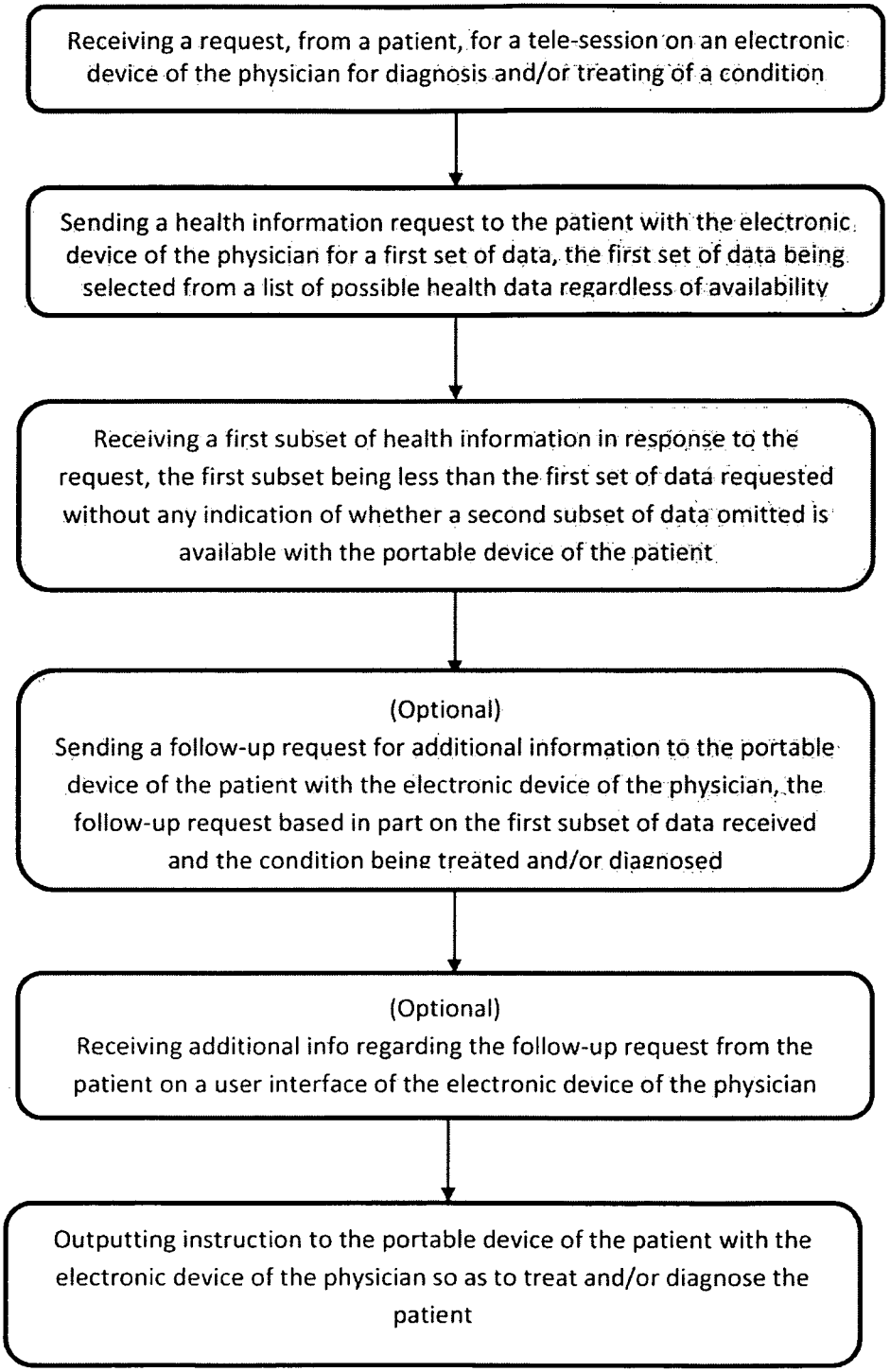
FIG. 11 is a flowchart of a method for managing patient information, in accordance with certain embodiments.

FIG. 11 illustrates an example method in accordance with the present invention that includes steps of: receiving a request, from a patient, for a tele-session on an electronic device of the physician for diagnosis and/or treating of a condition; sending a health information request to the patient with the electronic device of the physician for a first set of data, the first set of data being selected from a list of possible health data regardless of availability; receiving a first subset of the plurality of health data elements in response to the request, the first subset being less than the first set of data requested without any indication of whether a second subset of data omitted is available with the portable device of the patient; optionally, sending a follow-up request for additional information to the portable device of the patient with the electronic device of the physician, the follow-up request based in part on the first subset of data received and the condition being treated and/or diagnosed; optionally, receiving additional info regarding the follow-up request from the patient on a user interface of the electronic device of the physician; and outputting instruction to the portable device of the patient with the electronic device of the physician so as to treat and/or diagnose the patient.

Figure 12B:
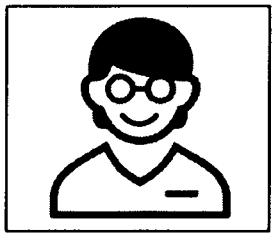

FIGS. 12A-12D illustrate a physician electronic device 402 (e.g. tablet device) and associated user interface during a tele-medicine session. FIG. 12A illustrates the initiation of the tele-medicine session by the patient. The physician then selects a set of data of the plurality of health data elements to request from patient. Since the physician electronic device is also coupled with the physician data system and the electronic medical record, once the session is initiated, the physician device 402 may populate portions of the user interface with known information from the physician data system and the electronic medical record, as shown in FIG. 12A. This information may also be useful in determining what data health elements to request, to avoid redundancies or if certain other conditions or medications are indicated from the electronic medical records.

FIG. 12B illustrates an option screen on the user interface that indicates possible types of health information that may be stored on or accessed with the patient's device 102. These options are not indicative of data that is present, but merely of possible types of data that may be present. The physician then selects the set of data to be requested. The physician may select the types of data individually, or by various categories or groupings of data, or according to pre-selected lists based on the specialty or the condition being treated and/or diagnosed. The physician then sends the information request and, in return, may receive a subset of data of the first set that was authorized by the patient, such as shown in FIG. 12C. The plurality of health data elements received from the patient may be displayed in a particular region of the user interface alongside with certain other information obtained from the physician data system for comparison. In some embodiments, the telemedicine platform allows third party applications as extensions providing semi-automated analysis to highlight relevant features and save time for both the patient and the physician.

In another aspect, results and analysis of data processed by third-party applications can be displayed side by side for easy comparison and validation. As shown in FIG. 12C, health data elements of the plurality may be processed data displaying a trend over time or averaged data, which may be received from the patient device as processed data, or alternatively, information received from the patient may be processed using one or more application on the physician device.

Figure 12D:
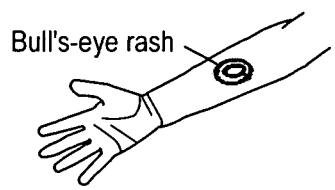

As discussed above, in response to receiving the first subset of data, the physician sends a follow-up request for visual inspection of the bug bite region. As shown in FIG. 12D, the physician receives a photo of the bug bite region, in response, such that the physician can determine a likely exposure to Lyme disease, discuss the diagnosis with the patient and prescribe medication accordingly and schedule a follow-up. Along with any physician notes, all physicians' orders are communicated back to the patient via secure channels. Clinical decisions support may be provided by third-party application on the physician device. Such applications may readily provide clinical guidelines, condition-specific order sets, focused patient data reports and summaries, drug-drug-interactions, diagnostic support and contextually relevant reference information (see textbook figure of typical target pattern of a tick bite exposure to Lyme disease shown in FIG. 12D).

In certain aspects, the above described system is further advantageous over conventional methods when applied during a patient visit to a physician within a clinic setting. In the clinic, health data elements from the patient's mobile device can be rapidly retrieved from the patient's devices using a common application (e.g. Physician Connect), which may also provide additional clinical decision support by use of third party applications, such as may be developed by various hospitals. Such third-party applications also may provide rapid clinical references information that may be discussed and shared with the patient. The system also allows the physician to readily take photos of areas of concern and associate the photos with the patient. The above described aspects provide improved efficiency as compared to conventional clinic visits since clinic time may be spent discussing diagnosis and treatment rather than interrogating patients for past conditions, medication history, allergies, and other background information.

In some embodiments, the user interface of the physician device may be configured to have separate areas designated for displaying information obtained from differing sources. For example as shown in FIGS. 12A-12B, medical record information may be displayed at top left, photo/video from the patient displayed at top right, health data elements from the patient device 102 displaced at center left, information from third-party applications on the physician device displayed on center right, and information from the physician data system can be stored at bottom. This display setup consolidates presentation of data and facilitates viewing and comparison by the physician so as to improve diagnosis and/or treatment by the physician. Upon the physician or patient ending the session, a record of the summary of the session may be provided and maintained securely in the patient device, as well as that of the physician.

Figure 13:
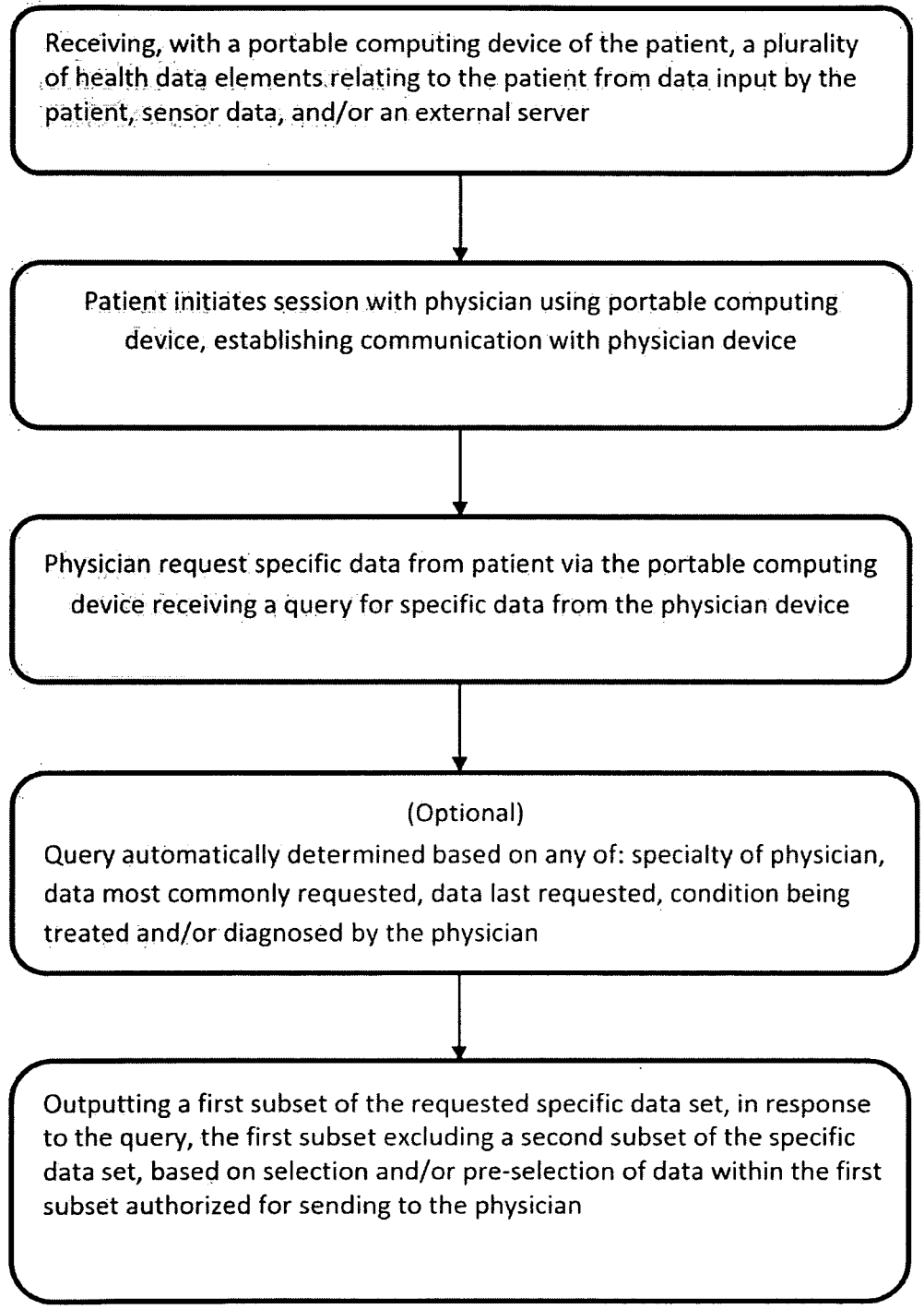
FIGS. 13-14 are flowcharts of methods of treatment and diagnosis using enhanced patient-physician communication, in accordance with certain embodiments.
Figure 14:
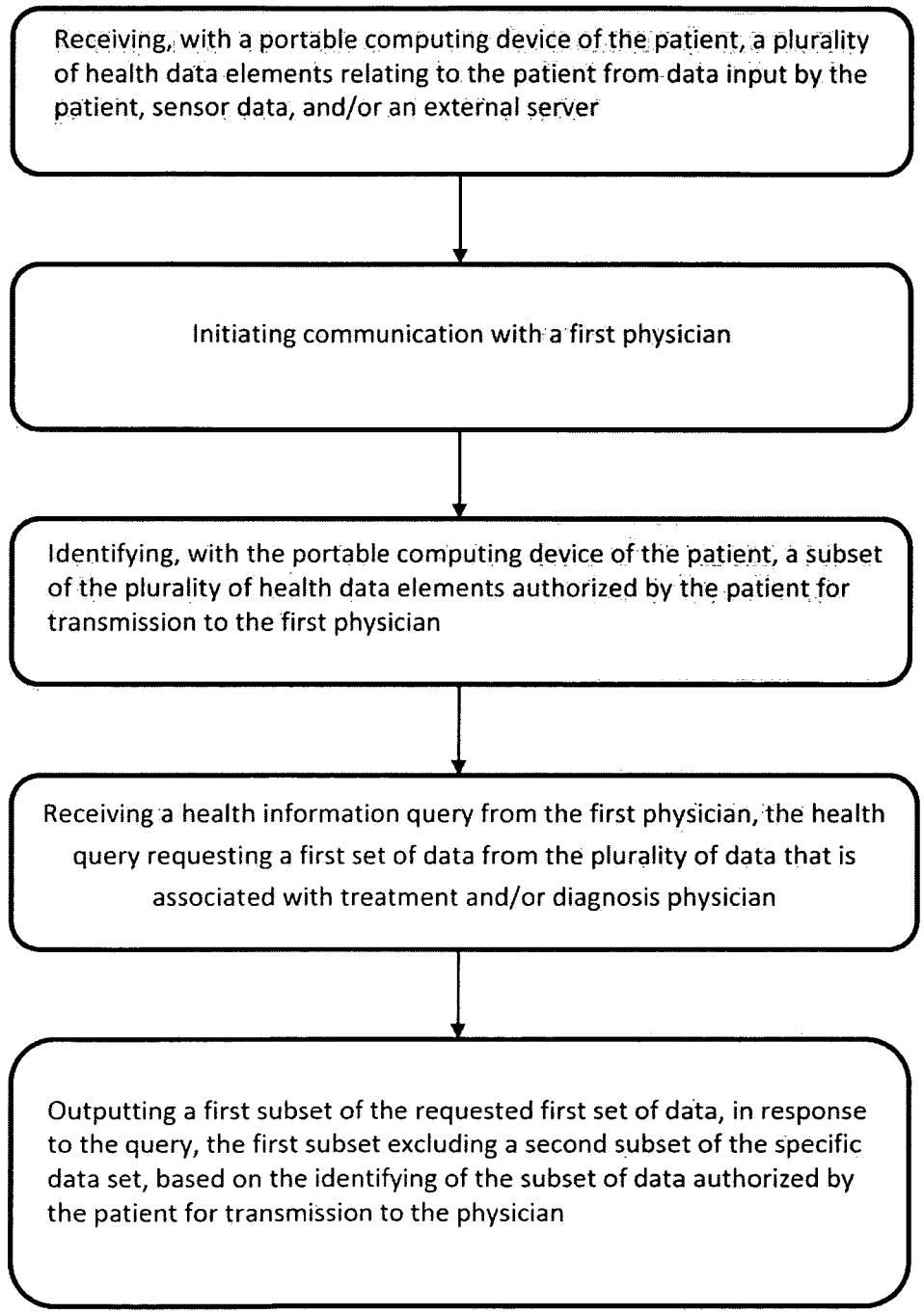

FIGS. 13-14 illustrate methods of treatment and/or diagnosis in accordance with the present invention. The method of FIG. 13 includes steps of: receiving, with a portable computing device of the patient, health information of the patient that includes health data elements input by patient and/or received from sensor or external server; patient initiates session with physician using portable computing device, establishing communication with an external device, such as a second computing device associated with the physician; the physician requests specific data from patient via the portable computing device receiving a query for specific data from the physician device; optionally, the query may be automatically determined based on any of: specialty of physician, data most commonly requested, data last requested, condition being treated and/or diagnosed by the physician; outputting to the physician, in response to the query, a first subset of the specific data and excluding a second subset of the specific data, based on selection and/or pre-selection of patient authorized data with the portable computing device.

The method of FIG. 14 includes steps of: receiving, with a portable computing device of the patient, health information of the patient that includes a plurality of health data elements; Initiating communication with a first physician; identifying, with the portable computing device of the patient, a first subset of the plurality of health data elements that is authorized by the patient for transmission to the first physician; receiving a health information query from the first physician, the health query requesting a first set of data from the plurality of health data elements that is associated with treatment and/or diagnosis physician; and outputting to physician, in response to query to facilitate treating and/or diagnosis of patient, a first subset of the requested first set of data that excludes a second subset of the first set of data, based on the identifying of the subset of patient authorized data from the plurality of health data elements.

Illustrative methods and systems for managing user device connections are described above. Some or all of these systems and methods may, but need not, be implemented at least partially by architectures such as those shown at least in FIGS. 1-14 above. While many of the embodiments are described above with reference to personal and/or health-related information, it should be understood any type of user information or non-user information may be managed using these techniques. Further, in the foregoing description, various non-limiting examples were described. For purposes of explanation, specific configurations and details are set forth in order to provide a thorough understanding of the examples. It is appreciated that the above examples may be practiced without certain specific details and that well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User devices (e.g., client devices) can include any type of general purpose personal computer such as, but not limited to, desktop or laptop computers running a standard operating system, as well as cellular, wireless, and/or handheld devices running mobile software and capable of supporting a number of networking and messaging protocols. These devices can also include other electronic devices, such as dummy terminals, thin-clients, gaming systems, or other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

The environment can include a variety of data stores and other memory and storage media as discussed above. These can reside in a variety of locations, such as on a storage medium local to (and/or resident in) one or more of the computers. Alternatively, the memory can be remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as desired.

The system and various devices may also include one or more software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

What is claimed is:

1. A method for facilitating treating and/or diagnosis of a patient in a live communication session, the method comprising:

prior to using a physician connection application for interfacing with a physician, receiving, with a first portable personal computing device of the patient, a plurality of health data elements of personal health information of the patient including health data elements automatically collected from one or more sensors of one or more sensor devices over a duration of time, the one or more sensor devices being communicatively coupled with the first portable personal computing device, wherein the plurality of health data elements are outside of any electronic medical record of the patient accessible by the physician, and wherein the one or more sensor devices are included in the first portable personal computing device and/or included within one or more wearable devices of the patient;

initiating the live communication session with a physician computing device of the physician with the first portable personal computing device of the patient through a physician connection application stored and executed on the first portable personal computing device of the patient, wherein the physician computing device comprises a corresponding physician connection application through which the live communication session is conducted;

receiving, with the first portable personal computing device via the physician connection application, a health information query from the physician during the live communication session, the health information query requesting a first set of data of the plurality of health data elements, the first set of data being associated with the treatment and/or diagnosis of the patient by the physician;

identifying, with the first portable personal computing device, a first subset of the plurality of health data elements that is selected by the patient for communication to the physician during the live communication session, based on a first user input received with the first portable personal computing device, wherein at least some of the health data elements of the first subset are automatically collected prior to initiating communication with the physician, wherein the plurality of health data elements are collected outside and separate from usage of the physician connection application;

authorizing release of the identified first subset of data to the physician, during the live communication session, based on a second user input received via the first portable personal computing device; and outputting to the physician during the live communication session, in response to the second user input the first subset of the first set of data that excludes a second subset of the first set of data from the first portable personal computing device to the physician computing device via the physician connection application so as to facilitate the treating and/or the diagnosis of the patient by the physician, wherein the plurality of health data elements, including the first subset output to the physician, are outside the electronic medical record of the patient.

2. The method of claim 1, the method further comprising: receiving a selection of the physician from a plurality of physicians displayed on a graphical user interface of the first portable device.

3. The method of claim 1, the method further comprising: receiving an input, with the first portable personal computing device, as to a condition for which treatment and/or diagnosis is desired.

4. The method of claim 1, wherein the plurality of health data elements includes any of: input or downloaded data, sensor data and laboratory values.

5. The method of claim 4, wherein input or downloaded data comprises data input by the patient.

6. The method of claim 1, wherein receiving the plurality of health data elements comprises receiving sensor data from the one or more sensors communicatively coupled with the first portable personal computing device, the sensor data relating to any of: activity level, activity tracking, respiration, body temperature, heart wellness data, hydration levels, perspiration, blood glucose, salinity, sleep cycles, posture, O2 levels, muscle engagement, or any combination thereof.

7. The method of claim 1, wherein the one or more sensors are included in one or more wearable devices that are wearable by the patient, each of the one or more wearable devices including a sensor that measures a health metric of the patient when worn by the patient.

8. The method of claim 7, wherein the health metric corresponds to any of an activity level, activity tracking, body temperature, heart wellness data, hydration levels, perspiration, blood glucose, salinity, sleep cycles, posture, O2 levels, muscle engagement, or any combination thereof.

9. The method of claim 7, wherein the health metric corresponds to blood glucose that is monitored by a wearable device such that the plurality of health data elements include blood glucose measurements obtained multiple times each day over the duration of time, the duration of time being one week or more, so as to facilitate treatment of diabetes.

10. The method of claim 1, wherein initiating communication with the physician comprises establishing communication with a second computing device associated with the physician, wherein communication is established remotely through a server and/or through near field communication.

11. The method of claim 10, wherein the first set of data is determined based on receiving of a categorical selection input by the physician with the second computing device, the categorical selection being selected from categories of: a specialty or sub-specialty, a medication or class of medication, and a condition or class of conditions for which the patient is being diagnosed and/or treated.

12. The method of claim 11, wherein the categories comprise the condition being diagnosed and/or treated, the condition including any of: a symptom, an injury, a disability, a disorder, a syndrome, an infection, dysfunction, pain or a disease.

13. The method of claim 11, wherein the categories comprise a class or type of medication grouped according to any of: chemical structure, mechanism of action, and purpose.

14. The method of claim 10, wherein the first set of data being requested is determined with the second computing device, at least in part, on one or more attributes of the patient, the attribute comprising one or more of: a risk factor associated with a condition being diagnosed and/or treated, a drug allergy, age, weight, gender, race, geographical location, ethnic background, a previously diagnosed condition, and a disease state.

15. The method of claim 1, wherein the first set of data includes any of: a patient's vital signs, one or more physiological measurements of the patient, a medication of the patient, a factor associated with a condition to be treated or diagnosed, or any combination thereof.

16. A system for facilitating treating and/or diagnosis of a patient by a live communication session, the system comprising:

a first portable personal computing device of the patient that is operable by the patient or an associated caretaker, the first portable personal computing device including a wireless communication module for transmitting to and receiving data from a physician;

a health information database accessible by the first portable personal computing device, wherein the health information database includes a plurality of health data elements of personal health information of the patient and including health data elements automatically collected from one or more sensors of one or more sensor devices over a duration of time by the first portable personal computing device communicatively coupled to the one or more sensor devices, wherein the plurality of health data elements are collected outside and separate from usage of a physician connection application, wherein the plurality of health data elements are outside of any electronic medical record of the patient accessible by the physician, and wherein the one or more sensor devices are included in the first portable personal computing device and/or included within one or more wearable devices of the patient; and a processor of the first portable personal computing device, the processor having a computer readable medium having stored thereon the physician connection application facilitating communication between the patient and the physician in a live communication session, the physician connection application having computer executable instructions configured to:
- initiate the live communication session with a physician computing device of the physician, through the physician connection application, using the communication module wherein the physician computing device comprises a corresponding physician application through which the live communication session is conducted;
- receive, through the physician connection application during the live communication session, a health information query from the physician requesting a first set of personal health data of the plurality that is associated with the treating and/or diagnosis by the physician;
- identify, from the plurality of health data elements, a first subset of the first set of data that is selected by the patient for communication to the physician, during the live communication session, based on the health information query and a first user input received with the first portable personal computing device, wherein the first subset includes at least some of the health data elements collected automatically prior to initiating communication with the physician;
- authorize release of the identified first subset of data to the physician, during the live communication session, based on a second user input received via the first portable personal computing device; and
- output to the physician during the live communication session, in response to the second input, the first subset of the first set of data that excludes a second subset of the first set of data from the first portable personal computing device to the physician computing device via the physician connection application so as to facilitate the treating and/or diagnosis of the patient by the physician, wherein the plurality of health data elements communicated are outside of the electronic medical record of the patient.

17. The system of claim 16, wherein the first portable device includes a user input, and the processor is further configured initiate communication with the physician in response to receiving a command input by the patient and/or a caretaker of the patient with the user input.

18. The system of claim 17, wherein the first portable personal computing device includes a graphical user interface and the processor is further configured to allow selection, with a user input, of the plurality of health data elements corresponding to the patient for whom communication with the physician is desired.

19. The system of claim 17, wherein the first portable personal computing device includes a graphical user interface and the processor is further configured to allow selection of the physician from a plurality of physicians displayed on the graphical user interface with the user input.

20. The system of claim 17, wherein the processor is further configured to display a plurality of physicians on a graphical user interface of the first portable device based on a condition desired to be treated and/or diagnosed received from the user input.

21. The system of claim 17, further comprising:
a graphical user interface of the first portable personal computing device, wherein the processor of the first portable personal computing device is configured to display, at least a portion of, the first set of data requested in the health information query and to allow selection of the first subset of the first set of data with the user input of the first portable personal computing device.

22. The system of claim 16, wherein the plurality of health data elements includes any of: an input or downloaded data, sensor data and laboratory values.

23. The system of claim 22, wherein input or downloaded data comprises data input by the patient.

24. The system of claim 16, wherein the one or more sensors are adapted to obtain sensor data and are communicatively coupled with the first portable personal computing device such that the plurality of health data elements include sensor data from the one or more sensors.

25. The system of claim 24, wherein the one or more sensors are configured to obtain sensor data relating to any of: activity level, activity tracking, respiration, body temperature, heart wellness data, hydration levels, perspiration, blood glucose, salinity, sleep cycles, posture, O2 levels, muscle engagement, or any combination thereof.

26. The system of claim 25, wherein the one or more sensors are configured to obtain sensor data over a duration of time and the processor is configured such that the sensor data is obtained automatically over the duration of time.

27. The system of claim 25 wherein at least some of the one or more sensors are incorporated into the first portable personal computing device.

28. The system of claim 24, wherein the one or more sensors include one or more wearable devices that are wearable by the patient, each including a sensor that measures a health metric of the patient when worn by the patient.

29. The system of claim 28, wherein the health metric corresponds to any of an activity level, activity tracking, body temperature, heart wellness data, hydration levels, perspiration, blood glucose, salinity, sleep cycles, posture, O2 levels, muscle engagement, or any combination thereof.

30. The system of claim 29, wherein the health metric corresponds to blood glucose that is monitored by a wearable device such that the plurality of health data elements include blood glucose measurements obtained multiple times each day over a duration of time, the duration of time being one week or more.

31. The system of claim 24, wherein the one or more sensors and the processor are configured such that the sensor data is automatically communicated to the first portable device for inclusion in the plurality of health data elements stored within the health information database.

32. The system of claim 24, wherein at least some of the plurality of health data elements are not specific to a health condition being treated and/or diagnosed by the system.

33. The method of claim 1, further comprising:
receiving an instruction to the patient, with the first portable personal computing device via the physician connection application during the live communication session, from the physician regarding the diagnosis and/or treatment.

34. The system of claim 16, wherein the processor of the first portable personal computing device is further configured to:
receive an instruction to the patient, with the first portable personal computing device via the physician connection application during the live communication session, from the physician regarding the diagnosis and/or treatment.

35. The method of claim 1, wherein the first user input is different from the second user input.

36. The system of claim 16, wherein the first user input is different from the second user input.

37. The method of claim 1, wherein the physician connection application of the first portable personal computing device has full access to all of the plurality of health elements collected, whereas the physician computing device has access to the first subset of data but not the excluded second subset of data.

38. The system of claim 16, wherein the physician connection application of the first portable personal computing device has full access to all the plurality of health elements collected and wherein the physician computing device is separately coupled with the electronic medical record of the patient.

* * * * *